(12) United States Patent
Vasilyev et al.

(10) Patent No.: US 11,097,090 B2
(45) Date of Patent: Aug. 24, 2021

(54) MECHANICAL ASSIST DEVICE

(71) Applicants: Children's Medical Center Corporation, Boston, MA (US); President and Fellows of Harvard College, Cambridge, MA (US)

(72) Inventors: Nikolay V. Vasilyev, Newton, MA (US); Pedro J. del Nido, Lexington, MA (US); Tonatiuh M. Lievano Beltran, Cuernavaca (MX); Erik A. Kraus, Hillsborough, NC (US); Nikhil Mehandru, Roslyn, NY (US); Evelyn J. Park, Rolling Hills Estates, CA (US); Conor J. Walsh, Cambridge, MA (US); Isaac Wamala, Jamaica Plain, MA (US); Markus Horvath, Cambridge, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 240 days.

(21) Appl. No.: 15/938,680

(22) Filed: Mar. 28, 2018

(65) Prior Publication Data
US 2018/0318484 A1   Nov. 8, 2018

Related U.S. Application Data

(63) Continuation of application No. 15/114,264, filed as application No. PCT/US2015/012886 on Jan. 26, 2015, now abandoned.
(Continued)

(51) Int. Cl.
*A61M 60/187* (2021.01)
*A61M 60/148* (2021.01)
(Continued)

(52) U.S. Cl.
CPC .......... *A61M 60/148* (2021.01); *A61B 5/283* (2021.01); *A61B 17/0401* (2013.01);
(Continued)

(58) Field of Classification Search
CPC .............. A61M 1/1003; A61M 1/1037; A61M 1/1046; A61M 1/1048; A61M 1/106;
(Continued)

(56) References Cited

U.S. PATENT DOCUMENTS 3,540,451 A * 11/1970 Zeman .............. A61M 39/0247
604/175
5,176,619 A    1/1993 Segalowitz
(Continued)

FOREIGN PATENT DOCUMENTS

EP    1 072 278 A2    1/2001
EP    1 016 377 B1    4/2006
(Continued)

OTHER PUBLICATIONS

Ching-Ping Chou and B. Hannaford, "Static and dynamic characteristics of McKibben pneumatic artificial muscles," Proceedings of the 1994 IEEE International Conference on Robotics and Automation, San Diego, CA, 1994, pp. 281-286 vol.1.*
(Continued)

*Primary Examiner* — Eugene T Wu
(74) *Attorney, Agent, or Firm* — Wolf, Greenfield & Sacks, P.C.

(57) ABSTRACT

Methods and apparatuses relate to an implantable device for providing contractile assistance to an organ. The device may include an actuator and anchors located on either side of the actuator. The anchors engage with oppositely positioned tissue walls of an organ chamber, and provide contractile assistance to the organ, repeatedly, at appropriate times. For example, the device may be implanted within the right
(Continued)

ventricle, anchored to the right ventricular free wall and the ventricular septum. The device may function to bring the opposing walls of the ventricle toward one another, synchronized with the pacing of the heart, resulting in an improved ejection fraction of blood from the chamber. In some embodiments, the actuator includes a bladder that is configured to contract upon receiving an inflow of pressurized fluid therein. When the fluid exits therefrom, the bladder relaxes back to an initial, extended state.

31 Claims, 27 Drawing Sheets

Related U.S. Application Data

(60) Provisional application No. 61/931,941, filed on Jan. 27, 2014.

(51) Int. Cl.
| | |
|---|---|
| A61B 17/04 | (2006.01) |
| A61B 5/283 | (2021.01) |
| A61M 60/40 | (2021.01) |
| A61M 60/50 | (2021.01) |
| A61B 17/00 | (2006.01) |
| A61M 60/122 | (2021.01) |
| A61M 60/268 | (2021.01) |
| A61M 60/857 | (2021.01) |

(52) U.S. Cl.
CPC .......... *A61M 60/187* (2021.01); *A61M 60/40* (2021.01); *A61M 60/50* (2021.01); *A61B 2017/00243* (2013.01); *A61B 2017/0404* (2013.01); *A61B 2017/0417* (2013.01); *A61M 60/122* (2021.01); *A61M 60/268* (2021.01); *A61M 60/857* (2021.01); *A61M 2205/0283* (2013.01); *A61M 2205/32* (2013.01); *A61M 2205/33* (2013.01); *A61M 2205/3303* (2013.01); *A61M 2230/005* (2013.01); *A61M 2230/04* (2013.01)

(58) Field of Classification Search
CPC ..... A61M 1/1068; A61M 1/122; A61N 1/057; A61N 1/0573; A61N 1/0575; A61N 2001/0578; A61N 2001/058; A61N 2001/0582; A61N 2001/059
See application file for complete search history.

(56) References Cited

U.S. PATENT DOCUMENTS

| | | | |
|---|---|---|---|
| 5,941,813 A | 8/1999 | Sievers et al. | |
| 6,030,335 A | 2/2000 | Franchi | |
| 6,206,895 B1 | 3/2001 | Levinson | |
| 6,221,092 B1 | 4/2001 | Koike et al. | |
| 6,221,902 B1 | 4/2001 | Malamas et al. | |
| 6,264,601 B1 | 7/2001 | Jassawalla et al. | |
| 6,299,575 B1 | 10/2001 | Bolling | |
| 6,673,009 B1 | 1/2004 | Vanden Hoek et al. | |
| 6,709,382 B1* | 3/2004 | Horner ................ | A61M 1/1068 600/16 |
| 6,868,291 B1 | 3/2005 | Bonner et al. | |
| 6,918,870 B1 | 7/2005 | Hunyor et al. | |
| 7,081,084 B2 | 7/2006 | Melvin | |
| 7,320,665 B2 | 1/2008 | Vijay | |
| 7,481,771 B2 | 1/2009 | Fonseca et al. | |
| 7,736,299 B2 | 6/2010 | Klenk et al. | |
| 7,811,318 B2 | 10/2010 | Yavorski et al. | |
| 7,850,729 B2 | 12/2010 | Melvin | |
| 7,878,966 B2 | 2/2011 | Jenson | |
| 8,366,743 B2 | 2/2013 | Zeng et al. | |
| 8,425,402 B2 | 4/2013 | Annest et al. | |
| 8,500,790 B2 | 8/2013 | Khairkhahan | |
| 8,979,750 B2 | 3/2015 | Van Bladel et al. | |
| 9,211,115 B2 | 12/2015 | Annest et al. | |
| 9,358,111 B2 | 6/2016 | Spence et al. | |
| 2002/0068849 A1 | 6/2002 | Schweich et al. | |
| 2003/0204205 A1 | 10/2003 | Sauer et al. | |
| 2005/0033396 A1* | 2/2005 | Ospyka ................ | A61N 1/059 607/130 |
| 2005/0096696 A1* | 5/2005 | Forsberg ............ | A61B 17/0057 606/213 |
| 2005/0228434 A1 | 10/2005 | Amplatz et al. | |
| 2006/0079736 A1* | 4/2006 | Chin ................ | A61B 17/0401 600/151 |
| 2006/0178550 A1* | 8/2006 | Jenson ................ | A61M 1/1053 600/16 |
| 2008/0064917 A1 | 3/2008 | Bar et al. | |
| 2009/0076547 A1 | 3/2009 | Sugimoto et al. | |
| 2009/0209999 A1 | 8/2009 | Afremov | |
| 2010/0016655 A1* | 1/2010 | Annest ............ | A61B 17/00234 600/37 |
| 2010/0137678 A1 | 6/2010 | Walsh et al. | |
| 2010/0228312 A1 | 9/2010 | White et al. | |
| 2012/0063864 A1* | 3/2012 | Hess ................ | F16B 39/24 411/326 |
| 2012/0245623 A1 | 9/2012 | Kariniemi et al. | |
| 2013/0304198 A1 | 11/2013 | Solem | |
| 2015/0025553 A1* | 1/2015 | Del Nido ............ | A61B 17/0401 606/151 |

FOREIGN PATENT DOCUMENTS

| | | | |
|---|---|---|---|
| WO | WO 2008/006002 A2 | 1/2008 | |
| WO | WO 2013/123388 * | 8/2013 | ............... A61F 2/24 |
| WO | WO 2013/123388 A1 | 8/2013 | |

OTHER PUBLICATIONS

E. Park et al., "An intraventricular soft robotic pulsatile assist device for right ventricular heart failure," 2014 40th Annual Northeast Bioengineering Conference (NEBEC), Boston, MA, 2014, pp. 1-2.*
Horvath, M.A., Wamala, I., Rytkin, E. et al. "An Intracardiac Soft Robotic Device for Augmentation of Blood Ejection from the Failing Right Ventricle". Ann Biomed Eng (2017) 45: 2222-2233.*
International Search Report and Written Opinion for Application No. PCT/US2015/012886 dated Apr. 15, 2015.
International Preliminary Report on Patentability for Application No. PCT/US2015/012886 dated Aug. 11, 2016.
[No Author Listed] Prevalence of Coronary Heart Disease—United States, 2006-2010. Centers for Disease Control and Prevention. https://www.cdc.gov/mmwr/preview/mmwrhtml/mm6040a1.htm [dated Oct. 14, 2011; last accessed Apr. 24, 2018].
Arnold et al., The engineer and the clinician: understanding the work output and troubleshooting of the HeartMate II rotary flow pump. Journal Thorac Cardiovasc Surgergy. Jan. 2013; 145(1):32-6.
Auger et al., Mapping right ventricular myocardial mechanics using 3D cine DENSE cardiovascular magnetic resonance. J Cardiovasc Magn Reson. Jan. 11, 2012;14(4): 1-9.
Chou et al., Static and dynamic characteristics of McKibben pneumatic artificial muscles. Proceedings of the 1994 IEEE International Conference on Robotics and Automation. 1994;1:281-6.
Cohn et al., Cardiac remodeling—concepts and clinical implications: a consensus paper from an international forum on cardiac remodeling. Behalf of an International Forum on Cardiac Remodeling. J Am Coll Cardiol. Mar. 1, 2000;35(3):569-82.
Haber et al., Three-dimensional systolic kinematics of the right ventricle. Am J Physiol Heart Circ Physiol. Nov. 2005;289(5):H1826-33.
Horvath et al., An intracardiac soft robotic device for augmentation of blood ejection from the failing right ventricle. Ann Biomed Eng. 2017;45(9):2222-2233.
Hsu et al., Mechanical circulatory support for right heart failure: current technology and future outlook. Artif Organs. Apr. 2012;36(4):332-47.

(56) References Cited

OTHER PUBLICATIONS

Hunt et al., 2009 Focused update incorporated into the ACC/AHA 2005 Guidelines for the Diagnosis and Management of Heart Failure in Adults: A Report of the American College of Cardiology Foundation/American Heart Association Task Force on Practice Guidelines Developed in Collaboration With the International Society for Heart and Lung Transplantation. J Am Coll Cardiol. Apr. 14, 2009;53(15):e1-e90.

Mishra et al., "Coapsys mitral annuloplasty for chronic functional ischemic mitral regurgitation: 1-year results." The Annals of Thoracic Surgery. Jan. 31, 2006;81(1):42-6.

Park et al., An intraventricular soft robotic pulsatile assist device for right ventricular heart failure. 40th Annual Northeast Bioengineering Conference (NEBEC). 2014:1-2.

Philen et al., "Variable Stiffness Adaptive Structures utilizing Hydraulically Pressurized Flexible Matrix Composites with Valve Control." 47th AIAA/ASME/ASCE/AHS/ASC Structures, Structural Dynamics, and Materials Conference. May 1-4, 2006.

Simon, Assessment and treatment of right ventricular failure. Nature Reviews Cardiology. Apr. 1, 2013;10(4):204-18.

Slaughter, et al., "Advanced heart failure treated with continuous-flow left ventricular assist device." New England Journal of Medicine. Dec. 3, 2009;361(23):2241-51.

Suzuki et al., Dynamic cardiomyoplasty using artificial muscle. J Artif Organs.2008;11(3):160-2.

Van Der Linde et al., "Birth prevalence of congenital heart disease worldwide." Journal of the American College of Cardiology. Nov. 15, 2011;58(21):2241-7.

Yang et al., Using contracting band to improve right ventricle ejection fraction for patients with repaired tetralogy of Fallot: a modeling study using patient-specific CMR-based 2-layer anisotropic models of human right and left ventricles. J Thorac Cardiovasc Surg. Jan. 2013;145(1):285-93, 293.e1-2.

\* cited by examiner

MECHANICAL ASSIST DEVICE

RELATED APPLICATIONS

This application claims the benefit under 35 U.S.C § 120 and is a continuation of U.S. application Ser. No. 15/114,264, filed Jul. 26, 2016, which is a national stage filing under 35 U.S.C. § 371 of International Application No. PCT/US2015/012886, filed Jan. 26, 2015 and entitled "MECHANICAL ASSIST DEVICE," which claims priority under 35 U.S.C § 119(e) to U.S. Provisional Application No. 61/931,941, filed Jan. 27, 2014 and entitled "MECHANICAL ASSIST DEVICE," the contents of each of which are incorporated herein by reference in their entireties.

FEDERALLY SPONSORED RESEARCH

This invention was made with government support under Grant No. W81XWH-15-1-0248 awarded by the National Institutes of Health. The government has certain rights in the invention.

GOVERNMENT LICENSE RIGHTS

This invention was made with government support under Grant no. W81XWH-15-1-0248, awarded by the U.S. Department of the Army. The government has certain rights in the invention.

BACKGROUND

1. Field

Aspects herein relate to mechanical assist devices for implantation in tissue and methods of use.

2. Discussion of Related Art

Heart failure is one of the leading causes of death worldwide. While a number of methods of treatment have been developed for various types of heart failure, the options for treating certain types of heart failure, such as right ventricular heart failure, are limited and can lead to severe complications.

For example, one existing method of treatment employs a continuous flow device having a tube through which blood flows and is actively pumped between the different chamber(s) of the heart. Not only does this device require open-heart surgery to implant, the device is not fully implantable within the chest cavity. That is, during use, the blood circulates both inside and outside of the body. Such a system is both invasive and cumbersome to operate. Further, use of such devices also require that anticoagulants (e.g., blood thinners) be incorporated within the circulated blood, so that clotting does not occur within the machine.

Another method of treatment involves placing an actuating jacket around the heart. The jacket surrounds the chamber of interest and compresses against certain regions to help pump blood from one chamber to another. However, by virtue of the jacket being in continuous contact with the heart and applying repeated compressive force to the heart, such a jacket may undesirably affect the external vasculature of the heart. For example, the jacket may detrimentally impinge on or damage blood vessels that nourish the heart.

SUMMARY

The inventors have appreciated that it would be advantageous to employ a device within certain regions of the body that mechanically assists contractile motion at the region(s) of interest, in an active manner. For example, an actuator may be anchored at opposing tissue wall locations of a chamber (e.g., right ventricle, left ventricle, right atrium, left atrium) of a heart. The actuator, along with the anchors to which the actuator is coupled, may be configured to assist in suitable contraction of the chamber, at appropriate times. For instance, the device may be suitably synchronized with the pacing of the heart, assisting in contraction of a chamber in which the device is implanted, so as to improve overall ejection of blood from the chamber.

The device may include anchors constructed to engage with or otherwise attach to respective locations of a tissue wall of an organ. An actuator may be coupled to the anchors and, in some embodiments, the actuator may be disposed between opposing anchors. In certain embodiments, the actuator may be configured to move the anchors relative to one another between a contracted state and an extended or relaxed state, in a repeated fashion. For example, the actuator may be caused to contract so as to draw the anchors and, hence, the respective tissue wall region(s) to which the anchors are engaged, toward one another.

In some embodiments, contraction of the actuator is caused by an inflow of fluid into an actuating bladder disposed between opposing anchors. After contraction, the actuator may relax back to its original non-contracted, more extended position so as to allow the anchors, and respective tissue wall regions, to move away from one another. In some embodiments, extension of the actuator occurs by allowing fluid to flow out of the actuating bladder, relaxing the actuator.

In an illustrative embodiment, a device for providing mechanical assistance to an organ is provided. The device includes a first anchor adapted to engage with a first wall region of the organ; a second anchor adapted to engage with a second wall region of the organ; and an actuator coupled with the first anchor and the second anchor, and configured to move the first and second anchors relative to one another repeatedly between a contracted position where the anchors are moved toward each other to draw the first and second wall regions of the organ toward each other and an extended position where the anchors are moved away from each other relative to the contracted position to move the first and second wall regions away from each other.

In another illustrative embodiment, a method of using a device for providing mechanical assistance to an organ is provided. The method includes engaging a first anchor with a first wall region of the organ; engaging a second anchor with a second wall region of the organ; and operating an actuator coupled with the first anchor and the second anchor to move the first and second anchors relative to one another repeatedly between a contracted position where the anchors are moved toward each other to draw the first and second wall regions of the organ toward each other and an extended position where the anchors are moved away from each other relative to the contracted position to move the first and second wall regions away from each other.

Various embodiments of the present invention provide certain advantages. Not all embodiments of the invention share the same advantages and those that do may not share them under all circumstances. Various embodiments described may be used in combination and may provide additive benefits.

Further features and advantages of the present invention, as well as the structure of various embodiments of the present invention are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
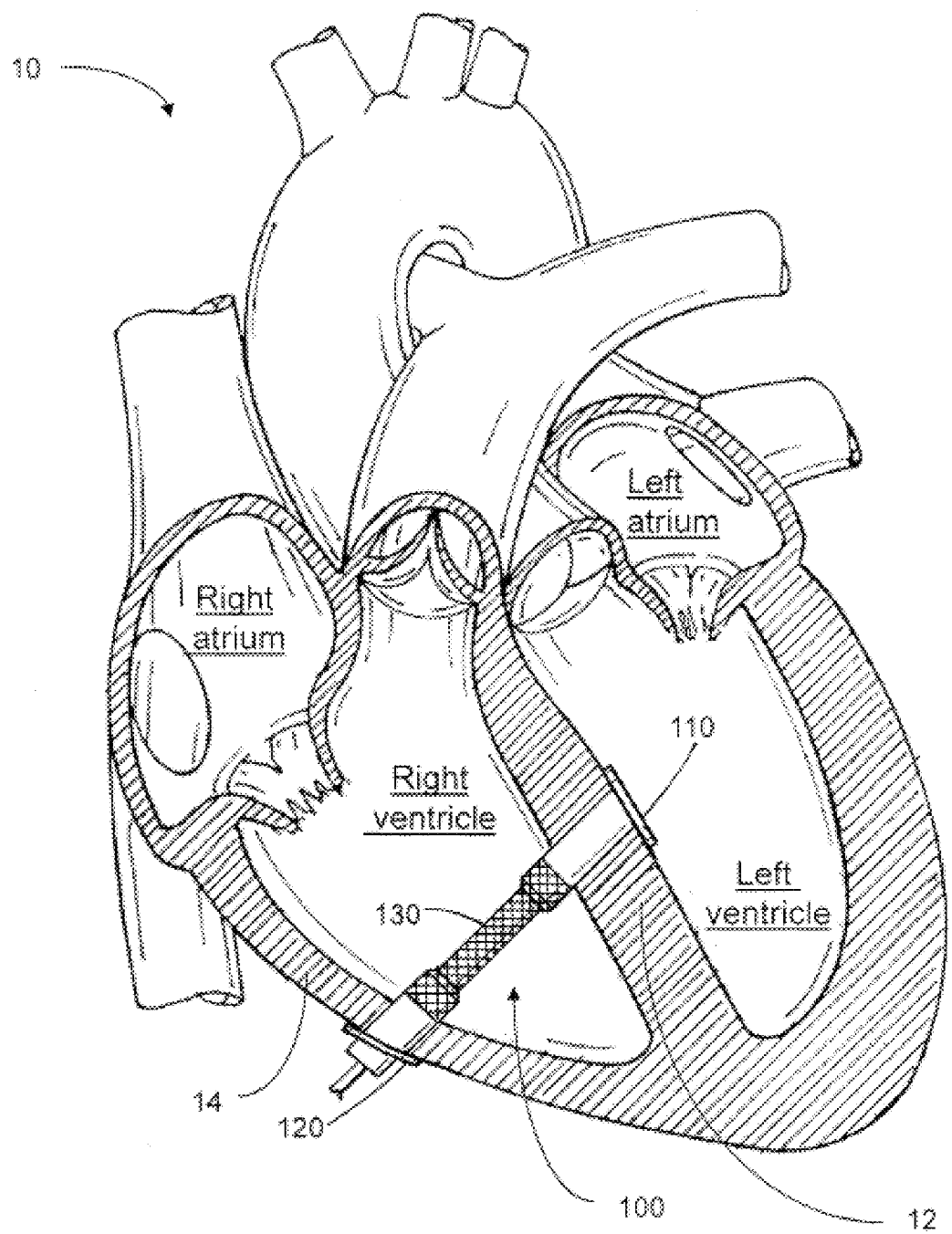
FIG. 1 shows a heart with a mechanical assist device implanted therein in accordance with some embodiments.

The present disclosure relates to an implantable device that may be configured to provide active mechanical assistance to the region (e.g., within an organ) at which the device is implanted. For example, the device may be implanted within a right ventricle of the heart, or left ventricle, and may provide a suitable degree of contractile assistance to the respective ventricle. Such contractile assistance may be coordinated with the natural cyclic pacing of the heart, so as to improve the overall ejection fraction of blood from the chamber in which the device is implanted.

The device may have a number of anchors for engaging with the tissue wall(s) of an organ. The device may also include an actuator coupled to each of the anchors. The actuator may cause the respective anchors to which it is coupled, and hence the tissue wall to which the anchors are engaged, to move back and forth relative to one another in a repeated motion.

In some embodiments, the actuator is located between two anchors, which are each engaged at respective tissue wall regions of the organ. For example, when the device is implanted in the right ventricle, one anchor may be engaged or otherwise attached at the ventricular septum, and another anchor may engage with the right ventricular free wall. Alternatively, if the device is implanted in the left ventricle, one anchor may be attached at the ventricular septum and an opposing anchor may engage with the opposite left ventricular wall.

As mentioned above, the actuator may be configured to contract, when appropriate, so as to pull the anchored tissue wall regions toward one another. The actuator may further be configured to extend, when appropriate, to allow the anchored tissue wall regions to relax back to their original position. For example, contraction and extension or relaxation of the actuator may be coordinated or otherwise timed to assist physiologic pumping of the ventricle, in a manner that restores or improves ejection of blood from the chamber and, hence, overall cardiac function.

Embodiments of mechanical assist devices in accordance with the present disclosure may exhibit a number of functional advantages. For example, as described above, conventional systems and methods that employ active or powered assistance in ejecting blood from the ventricle(s) often involve a flow through machine that continuously pumps blood through an artificial tube that runs through various chambers of the heart, typically implanted via invasive sternotomy and cardiac bypass procedures.

The above described flow through system substantially limits patient mobility, as the patient is required to be connected to a circulation system that pumps blood into the body, through the heart, and further pump blood out from the body. In contrast, mechanical assist devices described herein may be comparatively compact and portable. The device may be fully implanted, without need to circulate blood into and out of the body. Certain embodiments of the device may also be deployed through relatively non-invasive techniques, for example, through a transcatheter technique via a routine thoracotomy, as described further below, rather than through open heart surgery.

Further, when blood flows through a circulation system, the blood is constantly placed in physical contact with mechanical parts, such as bearings and impellers that may damage blood cells. Devices in accordance with the present disclosure may be free of abrasive mechanical components that may have a tendency to causes hemolysis.

In addition, by not requiring blood to flow through an artificial circulation system of any kind, as is often the case in conventional ventricular assist systems, the overall risk of blood clotting within an artificial vessel is substantially reduced. As a result, patients that employ devices in accordance with the present disclosure may not require anticoagulation medication regiments that would otherwise be necessary when using conventional techniques. Anticoagulation medication may have a tendency to inhibit or limit the normal process of healing by promoting bleeding, thus, it may be preferred for anticoagulation medication to be reduced or eliminated altogether from a patient treatment plan.

In accordance with aspects of the present disclosure, FIG. 1 shows a depiction of a mechanical assist device 100, implanted at a right ventricular location of the heart 10. The device 100 has a first anchor 110 and a second anchor 120, where the anchors located on opposite sides of the device. The device 100 further includes an actuator 130 coupled to each of the anchors 110, 120, and located therebetween. The first anchor 110 is engaged with or otherwise attached to the first wall, namely the ventricular septum 12, which is the wall between the right and left ventricles. The second anchor 120 is engaged to the second opposing wall, namely the right ventricular free wall 14. Accordingly, through the various anchor attachment points, the device 100 effectively forms a bridge between the ventricular septum 12 and the right ventricular free wall 14. This bridge provides a configuration through which the opposing walls of the right ventricle may be suitably assisted to contract and extend (or relax) in a repeated manner.

As discussed further below, the device may be deployed through a transcatheter arrangement. For example, during deployment within a right ventricle, the first anchor 110 may be inserted/pierced through the right ventricular free wall 14, guided through the chamber, and inserted/pierced through the ventricular septum 12. An anchoring portion of the first anchor 110 (e.g., radially extending flange, spiral coring member, etc.) may then be extended outward to hold the device in place, and not allowing the device to be inadvertently pulled back through the opening(s) formed during initial deployment. The second anchor 120 may have one or more anchoring portions (e.g., flange, threaded components, etc.) that may then be manipulated so as to firmly secure the device at an appropriate location of the right ventricular free wall 14.

Figure 2A:
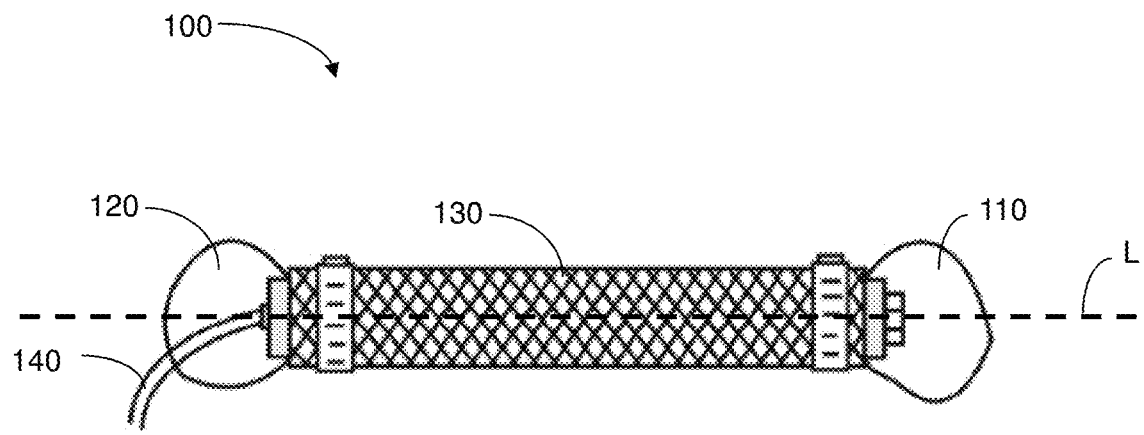
FIG. 2A depicts a mechanical assist device in an extended, relaxed state in accordance with some embodiments.
Figure 2B:
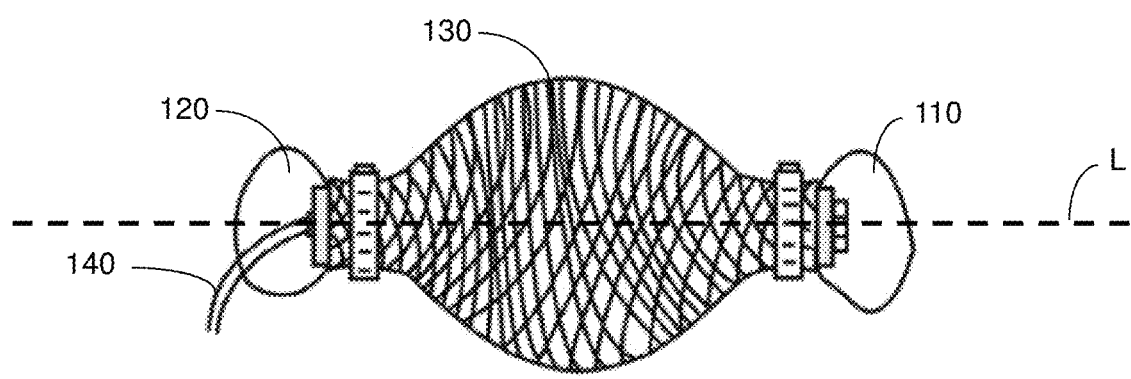
FIG. 2B illustrates the mechanical assist device of FIG. 2A in a contracted state in accordance with some embodiments.

FIGS. 2A-2B shows an embodiment of a mechanical assist device 100 including an actuator 130 coupled to and disposed between a first anchor 110 and a second anchor 120. The actuator 130 is further connected to a fluid line 140 which is configured to provide fluid to the actuator, so as to cause the actuator to contract. Such contraction results in a pulling force on the first anchor 110 and the second anchor 120 relative to one another. For example, as discussed further below, the fluid line 140 may provide a pressurized fluid to a mesh-guided bladder of the actuator 130, resulting in an overall contractile motion of the device.

For certain embodiments, the actuator 130 is constructed as an artificial muscle. For example, in the absence of an actuation signal (e.g., pressurized fluid injected into an actuating bladder), the actuator may conform to a relaxed, extended state. Though, when subject to an appropriate actuation signal, the actuator may suitably conform to a contracted state. The extended and contracted states are both appropriate for mechanically assisting pumping of blood through the chamber.

FIG. 2A depicts the device 100 to be in an extended state, where the actuator 130 exerts little to no force on the first and second anchors 110, 120. In some embodiments, the fluid line 140 provides little to no pressurized fluid flow to a compartment (e.g., mesh-guided bladder) of the actuator 130. Accordingly, the actuator remains in a relaxed, extended state.

FIG. 2B shows the device 100 to be in a contracted state, where the actuator 130 causes relative movement of the first anchor 110 and the second anchor 120 toward one another. As shown, the actuator 130 is contracted or otherwise shortened along a longitudinal axis L of the device, pulling the first and second anchors 110, 120 closer together. As further shown, a portion of the actuator 130 extends outward radially from the longitudinal axis L. In some embodiments, the fluid line 140 provides an adequate amount of pressurized fluid flow to the compartment of the actuator 130, resulting in appropriate contraction of the actuator.

As a result, in certain embodiments, upon contraction, the actuator may form an inflation profile, where the largest cross-sectional diameter is formed at the middle of the actuator and the smallest cross-sectional diameter arises at opposing ends of the actuator. It can be appreciated that the actuator may form any suitable shape and is not required to have the above described inflation profile. That is, upon contraction, the actuator may be form a profile that is irregular in nature, where the largest and/or smallest cross-sectional diameter(s) may be formed at one or more locations other than the middle of the actuator. For example, the actuator may form a sinusoidal or hour-glass shaped profile upon contraction.

While for some embodiments, the actuator may be substantially straight, for certain embodiments, the actuator is not straight. That is, the actuator may have a curved profile, or may be bendable upon actuation. For instance, the actuator may be relatively straight prior to actuation and, upon actuation, may exhibit a curved configuration. Or, the actuator may be curved before and after actuation. Accordingly, the separate tissue wall regions to which the device is attached are not required to be located directly opposite one another, as the device may accommodate for variations in the location(s) at which the device engages with the organ.

In certain embodiments, the actuator 130 of the device 100 is constructed as a pneumatic artificial muscle. For example, the actuator 130 includes a compartment, such as a bladder configured to receive an inflow of fluid (e.g., liquid, gas, etc.), via the fluid line 140. A bladder may employ a membrane, elastomeric pouch, or other suitable material, that defines a substantially enclosed space therein, where the material stretches or otherwise deforms in an appropriate manner when a sufficient amount of pressurized fluid enters therein.

The actuator 130 may further include a mesh surrounding the compartment. The mesh may be constructed so as to suitably confine the compartment and guide the overall shape of the compartment as fluid enters into and exits from the compartment. The mesh may be include any suitable material arranged in an appropriate configuration, such as wires or polymers arranged in a braided or netted formation. The mesh may include a woven or non-woven fabric, string, polymer (e.g., polyester) or metal mesh, or any other suitable material.

The mesh, compartment, or combination thereof, may be constructed in such a manner so as to contract or extend based on whether the compartment is filled with fluid. In some embodiments, the actuator is constructed as a McKibben actuator, which includes an inflatable bladder constrained by a mesh. When the bladder is filled with a fluid, depending on the pressure and amount of the fluid within the bladder, the actuator contracts appropriately. Hence, inflation of the bladder results in active contraction thereof, and deflation of the bladder results in active relaxation of the actuator to an extended state.

Turning back to the figures, when the compartment receives an adequate amount of fluid, the compartment actively alters in configuration from an extended state, as shown in FIG. 2A, to a contracted state, as shown in FIG.

2B. That is, in entering the contracted state, the compartment suitably contracts along the longitudinal axis L, and suitably expands along a radial direction relative to the longitudinal axis L.

Conversely, when the fluid within the compartment exits therefrom, the compartment relaxes and returns back to the extended state. At this point, the compartment extends along the longitudinal direction and contracts in the radial direction, reverting back to its original state. In some embodiments, the cross-sectional diameter or width of the compartment is substantially uniform when the actuator is in a relaxed, deflated state.

In some embodiments, a pumping apparatus may be provided to force fluid into and out of the compartment, for example, through the fluid line 140. For example, when the actuator is to be contracted, the pumping apparatus increases the overall pressure of fluid within the fluid line and the fluid is forced into the compartment. Though, when the actuator is be extended, the pumping apparatus decreases the overall pressure, in some cases, forming a vacuum within the fluid line so that fluid is pulled out of the compartment.

Any suitable fluid may be employed. In certain embodiments, the fluid may be liquid, such as water, saline, hydraulic fluid, oil, colloidal solution, emulsion, suspension, amongst others; or, the fluid may be gaseous, for example, air, argon, helium, carbon dioxide, nitrogen, etc. The fluid may have solid-like properties, for example, the fluid may be gel-like or may include a plurality of small particles.

A fluid reservoir supplying pressurized fluid to the compartment is optionally provided between the fluid line 140 and the compartment of the actuator 130. The pumping apparatus and fluid reservoir may each be located at any suitable location. That is, upon implantation of the device 100, either the pumping apparatus, the fluid reservoir, or both, may be suitably located within or outside the body. For example, if located within the body during use, the pumping apparatus and/or fluid reservoir may be disposed within or otherwise supported by a biocompatible housing. Or, the pumping apparatus and/or fluid reservoir may be located outside of the body during use. In some embodiments, the reservoir is constructed of an inert/nonleaching biocompatible material which, in some cases, may serve to separate the actuating fluid from the external environment. In certain embodiments, the reservoir may be hermetically sealed from the external environment.

Flow of fluid into and out of the compartment may be regulated in any suitable manner. In some embodiments, a valve arrangement may be provided between the compartment and the fluid line. For example, when it is determined that the actuator is to contract, the valve(s) regulating flow to and from the compartment may be opened so as to allow fluid to enter therein. When it is determined that the actuator is to relax or extend, the valve(s) may also be open, yet to permit fluid to exit therefrom. Between periods in which the actuator actively contracts or extends, the valve(s) may fully or partially close, allowing for appropriate regulation of the amount of fluid flow to and from the compartment, which may affect the degree in which the device is actuated. Valve arrangements may be used in combination with a system for supplying fluid to and removing fluid from the device, for example, a pump, vacuum, tubing, fluid reservoir, etc. It can be appreciated that any suitable type of valve (e.g., pneumatic, hydraulic, electrical, mechanical, etc.) may be employed in such valve arrangements, along with appropriate fluid flow components.

It can be appreciated that, for certain embodiments, actuators other than a pneumatically or hydraulically activated actuator may be employed. That is, the actuator may include one or more materials that actuate upon application of an appropriate stimulus or signal. For example, the actuator may include an electroactive polymer, which changes shape upon application of an electric field; alternatively, the actuator may include a suitable shape-memory alloy (e.g., nitinol), or other material that exhibits a conformational change upon exposure to an appropriate stimulus/signal. It can be further appreciated that other components that may undergo conformational changes, such as the anchors of the device, may also employ any suitable material or mechanism through which their shape is changed, such as those materials or compositions described above.

Figure 3A:
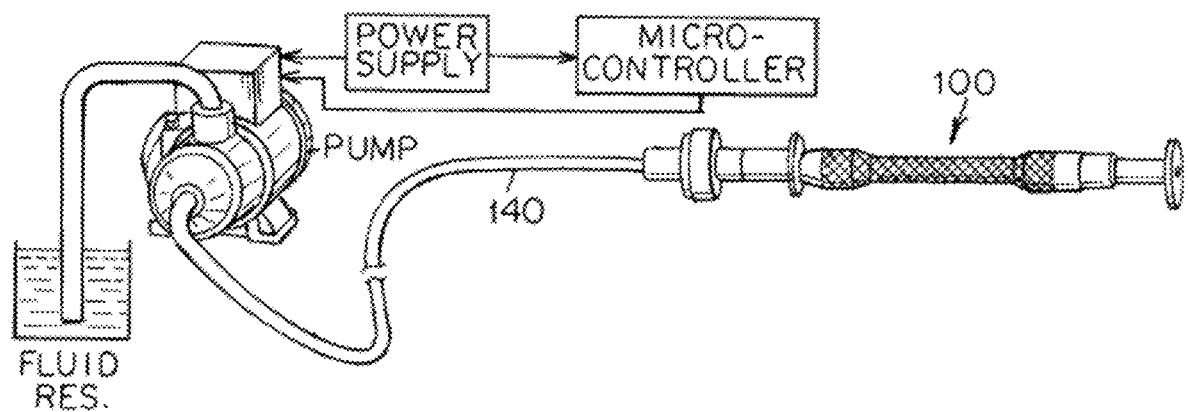
FIGS. 3A-3B depict a mechanical assist device in accordance with some embodiments.
Figure 3B:
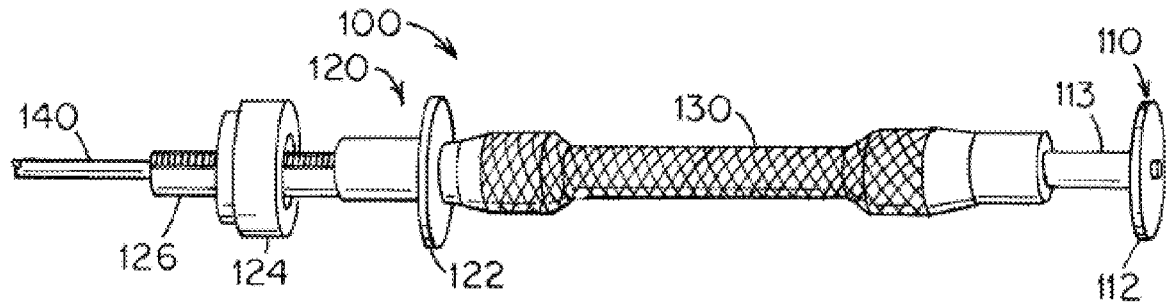

FIG. 3 depicts an illustrative embodiment of a mechanical assist device 100 in accordance with the present disclosure. The device 100 includes first and second anchors 110, 120, disposed opposite one another, and an actuator 130 coupled to the anchors and located therebetween.

Each of the anchors of the device, when appropriately deployed, may enable the actuator to be secured to the respective tissue wall(s) of the organ in which the device is implanted.

In some embodiments, upon suitable deployment, the anchors form a seal with the respective wall region of the organ. That is, not only are the anchors firmly attached to the respective tissue wall(s), the anchors also form a seal so as to prevent leakage through the wall via the opening(s) through which the anchors are implanted. In some embodiments, a suture configuration, such as a purse string suture may be employed, in combination with the respective anchor(s), so as to form a suitable seal between the opening of the tissue wall formed during deployment, and the anchors. A purse string suture may be a surgical suture passed as a running stitch in and out along the edge of an opening in such a way that when the ends of the suture are drawn tight, the opening is closed like a purse, obstructing fluid from flowing therethrough.

Figure 10A:
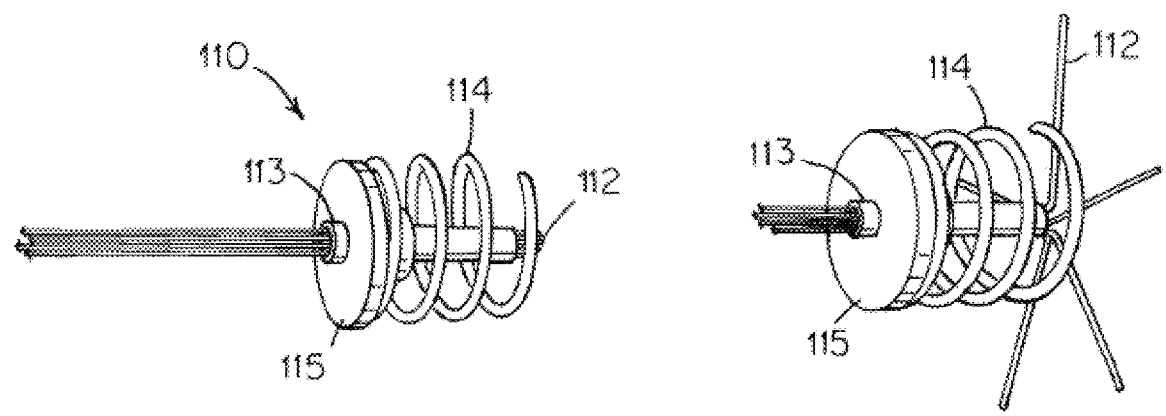
FIGS. 10A-10B depict anchors of mechanical assist devices in accordance with some embodiments.
Figure 10B:
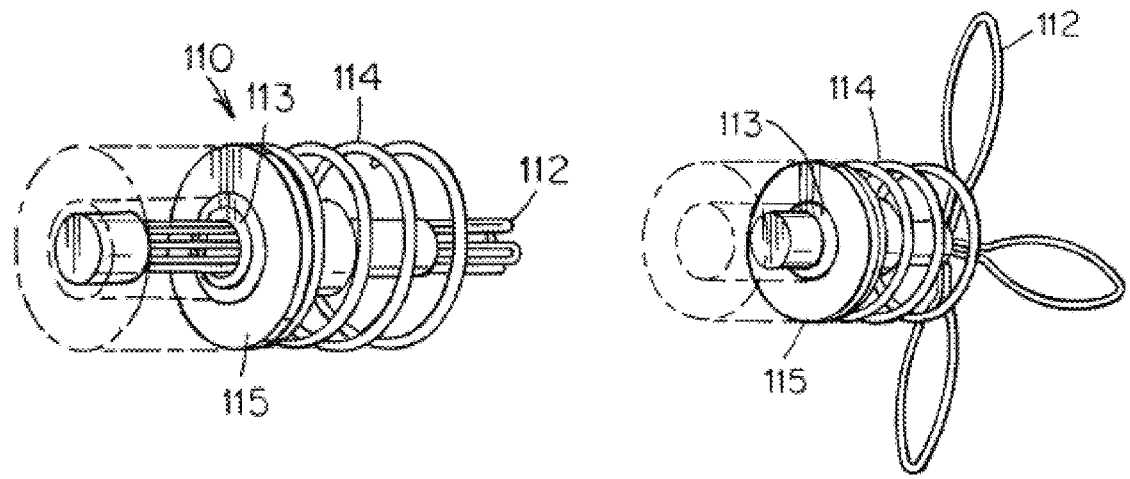

In this embodiment, the first anchor 110 includes an anchoring flange 112, which is effective to prevent the device from being inadvertently pulled back through the ventricular septum. While the first anchor 110 is shown in FIG. 3 to have a round shaped anchoring flange 112, it can be appreciated that the first anchor 110 may employ any suitable arrangement. For example, the flange 112 may be T-shaped, or have radially extending rods or petals, as shown in FIGS. 10A-10B.

For example, the first anchor 110 may include a flange 112 that is initially stored within a delivery tube 113 and is extendable therefrom during deployment. Further, deployment of the anchor may be reversible. That is, the flange 112 may be retracted back into the delivery tube, for example, at a later time for replacement or removal of the previously implanted device. In certain embodiments, upon implantation of the device, after the appropriate tissue wall (e.g., ventricular septum) is pierced, a portion of the anchor may be extended along the inner surface of the adjacent chamber (e.g., inner wall of left ventricle) so as to form a flange that serves to firmly secure the first anchor 110 in place. When it is desired for the device to be removed, the respective flange may be retracted back into the delivery tube of the device, so as to allow the device to be removed from the tissue wall.

Alternatively, as shown in FIGS. 2A-2B, the first anchor 110 may include an inflatable anchoring bladder that deploys into a flange, which is separate from the mesh-guided bladder of the actuator 130. The anchoring bladder may be flexible or pliable when in a deflated state, yet may become relatively rigid when suitably filled with a pressurized fluid. In some embodiments, upon inflation, the anchoring bladder exerts a radial force against the tissue wall for suitable attachment thereto.

In some embodiments, the anchoring bladder may exhibit a rounded or bulged profile when inflated, rather than having any sharp edges. In contrast, if a deployed anchor has sharp edges, such edges may be prone to damaging surrounding tissue(s).

In certain embodiments, an anchoring bladder may be coupled to a dedicated pressure line, separate from the fluid line 140 which is used to inflate and deflate the actuating bladder.

As discussed herein with respect to management of fluid flow to and from the actuator, an optional valve may also be provided to regulate fluid flow to and from an anchoring bladder, so as to mitigate against any undesirable fluid leakage. For example, upon appropriate filling of the bladder, the valve may be shut to prevent backflow of fluid from the bladder.

Similar to that of the actuating bladder, any suitable fluid, liquid, gas, or other, may be used to inflate an anchoring bladder.

In the embodiment of FIG. 3, the second anchor 120 includes a flange 122, a first fastening component 124 and a second fastening component 126. In some embodiments, the first fastening component 124 is an anchoring cap, and the second fastening component 126 is a track, ratcheting ladder, threaded bolt or other surface upon which the first fastening component may engage or be otherwise attached.

The flange 122, which is optional, may provide support for the device on the inner side of the chamber of implantation. The flange 122 may be provided in accordance with any suitable configuration(s), such as those described above with respect to the flange 112 of the first anchor 110. For example, the flange 122, initially stored within a delivery tube, may be reversibly extendable and retractable, allowing for removal or replacement of the device.

In some embodiments, the position of the flange 122 may be adjusted along the length of the device, for example, along the second fastening component 126, similarly to that described below with respect to the first fastening component 124, along another slidable, ratcheted or threaded region, or in any other suitable manner. Alternatively, the flange 122 may include an anchoring bladder inflatable via an appropriate pressure line. It can be appreciated that for certain embodiments, the flange 122 is not required to be incorporated along with the second anchor 120.

In certain embodiments, the first fastening component 124 and the second fastening component 126 have surfaces that are mechanically complementary to one another such that the position of the first fastening component 124 along the second fastening component 126 can be adjusted to a desired location, and set firmly in place. For example, the first fastening component 124 and the second fastening component 126 may be threaded in a complementary manner so that the first fastening component 124 may be suitably screwed on to the second fastening component 126 up to a certain location. Accordingly, the first fastening component 124 may be provided as a threaded nut and the second fastening component 126 may be a threaded bolt on which the nut may be fastened or otherwise secured. For some embodiments, the second fastening component 126, which may be a threaded bolt, may be hollow or may otherwise have a space through which the fluid line 140 may access the actuator 130.

An anchoring cap and track may serve as suitable complementary fastening components. Though, it can be appreciated that an anchoring cap and track, as presented herein, are not required aspects of the present disclosure, as other arrangements of suitable fastening components may be used.

In some embodiments, the grooves of the threaded bolt and nut may be arranged so as to create resistance to twisting at appropriate locations along the device. For example, the resistance to twisting between the two threaded components may be greater at locations where the anchoring cap pushes up against the tissue wall, so as to form a secure attachment thereto. Accordingly, such resistance to twisting would mitigate against accidental loosening or dislodging of the device from the tissue wall. To retract the device from engagement with the tissue wall, at the very least, this resistance would have to be overcome.

The degree of resistance between threaded components may be modulated, for example, by varying the spacing between the inner surface of the threaded nut and the outer surface of the threaded bolt. As the spacing between these surfaces is decreased, the overall relative contact (e.g., number of mutual contact points, area of mutual contact, etc.) between the components is increased, which increases resistance to twisting therebetween. Conversely, increasing the spacing between the surfaces may decrease the overall relative contact between the components, resulting in comparatively less resistance to loosening of the components with respect to one another.

As noted above, the optional flange 122 may include a threaded or otherwise grooved configuration that allows for the flange 122 to be adjusted along an appropriate portion of the length of the device, for example, along the second fastening component 126. Such an arrangement may be similar to that discussed above with respect to arrangements between the various fastening components.

In some embodiments, the second fastening component 126 may include a track having a ratcheted configuration that allows for movement of the first fastening component 124 toward the actuator, for tightening attachment of the overall anchor 120 to the tissue wall. A ratcheted configuration between the second fastening component 126 and first fastening component 124 is one-way or two-way. In some cases, the second fastening component 126 may also include a lumen through which the fluid line 140 may have access to the actuator 130.

When engaged with the tissue wall(s), the anchors 110, 120 may be remain suitably attached to the respective tissue wall(s) despite continuous, vibrational movements or disturbances that arise from the beating heart, or other constant or sudden motion. In some embodiments, a suitable locking mechanism may be provided for the anchor(s) on either tissue wall to be firmly secured. For example, to form a suitable attachment to the tissue wall, the first fastening component 124, or other component (e.g., flange 122), may have protruding pegs that may be engaged with one or more complimentary slots of the second fastening component 126, so as to form a locked configuration. Such a locking arrangement may be reversible, for example, the first fastening component 124 may be removed by retracting the protruding peg(s) from the slot.

For the device to be effective in ejecting fluid (e.g., blood) from the chamber (e.g., ventricle), adequate portions or surface area of the respective tissue wall regions must be actuated back and forth with respect to one another. That is, it may be preferable for the anchors of the device to cause a sufficient area of the respective tissue wall regions to exhibit contractile behavior. For example, the flanges 112, 122 of the anchors may span a relatively wide area so as to draw enough tissue inward to assist chamber contraction in an adequate manner. Or, multiple mechanical assist devices may be deployed, and arranged in a parallel configuration so as to cause enough of the tissue wall to contract in order to be effective in ejecting fluid from the chamber.

Figure 4A:
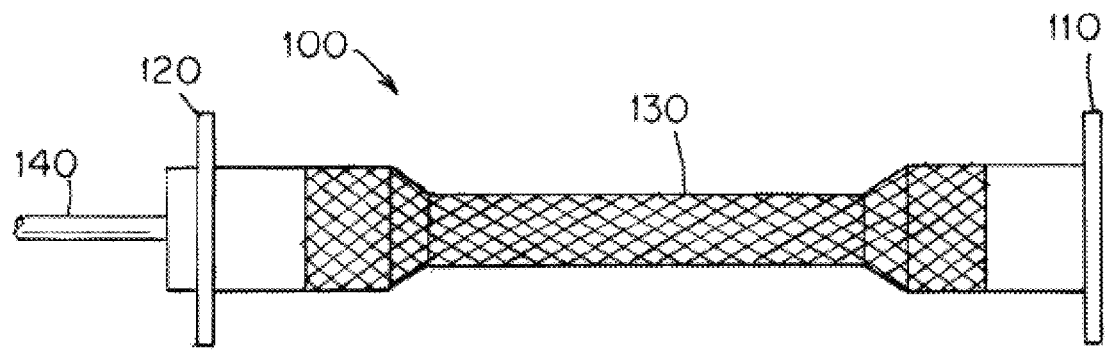
FIGS. 4A-4B shows a mechanical assist device in extended and contracted states in accordance with some embodiments.
Figure 4B:
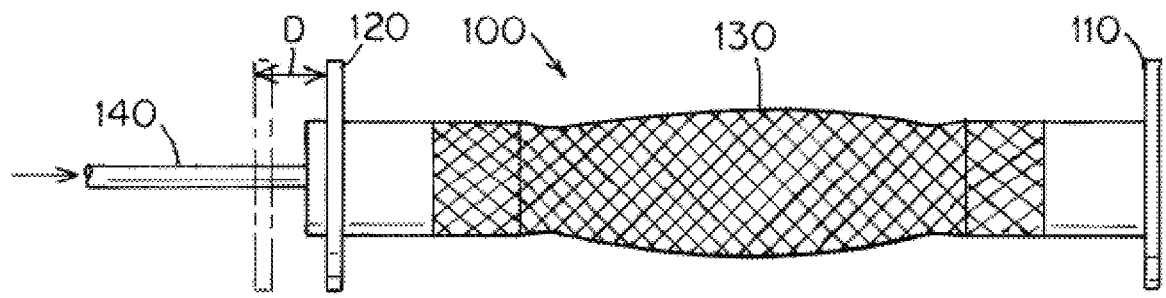

In the embodiment of FIG. 3, the actuator 130 includes an inflatable bladder and a mesh surrounding the bladder. Upon inflation of the bladder, the mesh guides resulting axial and radial motion of the bladder. FIG. 4 shows an illustrative embodiment of the device 100 in extended and contracted states, respectively. As depicted, in the extended state shown in the upper portion of FIG. 4, the actuator 130 is relaxed so that the bladder has a substantially uniform cross-sectional area along its length. Though, upon contraction, shown in the lower portion of FIG. 4, the actuator 130 shortens a distance D along the longitudinal axis of the device. Such contraction brings the first and second anchors 110, 120 and, hence, the wall regions to which the anchors are attached, toward one another. As further shown, during contraction of the actuator, the bladder also bulges out radially. In some cases, as shown, the device may form a slight bend, though relatively insubstantial.

Various components of the device may be coated or made of a biocompatible material. For example, the first anchor, the second anchor and/or the actuator may be coated with or at least partially made up of a suitable material that allows for the device to be appropriately integrated or otherwise implanted within the body at the site of an organ without detrimental biological effect(s). Any surface or component of the device (e.g., anchors, actuator, etc.) may be coated or conditioned with various treatments to achieve beneficial therapeutic effects such as to promote occlusion, thrombosis and/or initiate formation of tissue that naturally integrates the component(s) with the surrounding tissue. Or, the surface or component itself may be made up of a material that permits such beneficial effect(s). For example, at least a portion of the anchor(s) may include a material that promotes integration and/or attachment of the device to the corresponding tissue wall(s).

Such coatings and/or materials of the device may include any suitable biocompatible composition. In some embodiments, the anchor(s) and/or actuator may be coated with, or at least partially made up of, a stretchable biocompatible elastomer, such as a silicone-based polymer (e.g., ECO-FLEX®, ELASTOSIL®, etc.).

In some embodiments, the device may include a coating and/or material that allows for elution of a bioactive agent. That is, the implanted device may have a region that provides for controlled release of one or more therapeutic substances, for example, amino acids, vaccines, antiviral agents, nucleic acids, gene delivery vectors, interleukin inhibitors, immunomodulators, neurotropic factors, neuroprotective agents, antineoplastic agents, chemotherapeutic agents, polysaccharides, anti-coagulants, collagen-based material, antibiotics, analgesic agents, anesthetics, antihistamines, anti-inflammatory agents, vitamins, therapeutic stem cells, amongst other materials, or any suitable combination thereof. For example, a portion of the coating and/or material may include a bioresorbable material that allows for the bioactive agent to be dispersed. In some embodiments, at least one of the anchors or other component(s) of the device may be configured for controlled release of stem cells, or another bioactive composition, at or near the tissue wall of a patient suffering from a condition, such as right or left ventricular myocardial infarction and/or heart failure.

In some cases, when implanted, the anchor(s) may come into contact with a tissue wall on one side, and may come into contact with blood on an opposite side. Accordingly, for certain embodiments, the side of the anchor that faces the tissue wall (e.g., ventricular septum) may be coated with a material that promotes biointegration, and the side of the anchor that faces the chamber, and is hence exposed to blood, may be coated with materials that provide anti-cell proliferation, anti-thrombogenic, anti-immunogenic properties.

Mechanical assist devices in accordance with the present disclosure may be deployed by any suitable technique. Aspects described herein provide for embodiments of the device to be delivered in a minimally-invasive manner. For example, rather than open heart surgery, the device may be deployed via a transcatheter procedure.

FIGS. 5A-5F show an example of an implantation procedure of an embodiment of a mechanical assist device. The procedure involves a thoracotomy where small incisions are made into the pleural space of the chest for access to the heart for insertion of a catheter 200. Here, the device 100 is arranged to fit within a catheter housing 210 (e.g., insertion cannula), and is deployed through the catheter into the right ventricle of the heart 10. Upon implantation, the device is anchored at opposite ends, to the ventricular septum 12 and the right ventricular free wall 14.

Figure 5A:
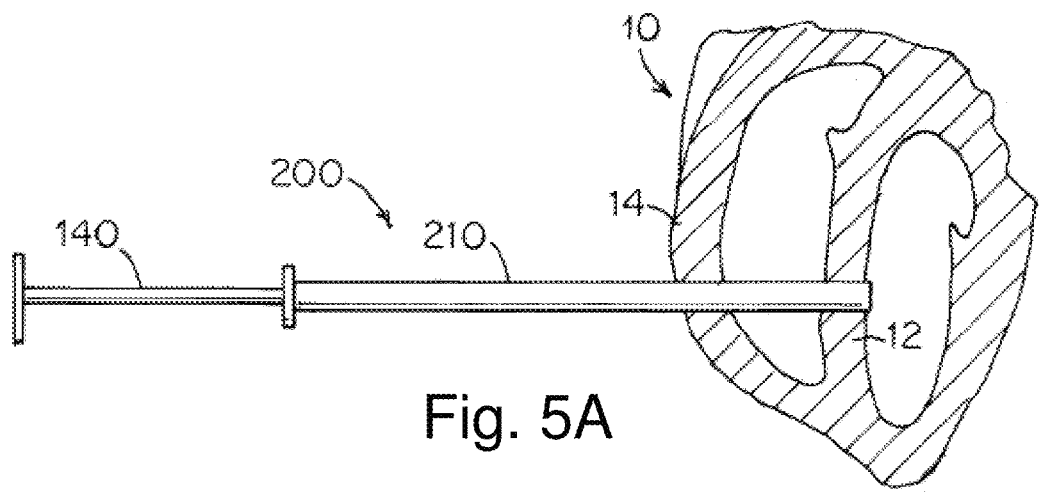
FIGS. 5A-5F show implantation of a mechanical assist device in accordance with some embodiments.

The catheter 200 may include a relatively sharp distal end (e.g., pointed pick) for piercing and penetrating a tissue wall. In this procedure, the catheter is guided toward the right ventricle of the heart 10. The distal end of the catheter punctures the right ventricular free wall 14 so as to allow entry of the catheter, with the mechanical assist device 100 disposed within its housing 210, into the right ventricle. In some embodiments, the opening created by the puncture is relatively small (e.g., less than 2 mm in diameter), just large enough to feed the device therethrough. As shown in FIG. 5A, the catheter 200 is guided further into the right ventricle, and further punctures the ventricular septum 12, allowing the device 100 to migrate further into the left ventricle.

Figure 5B:
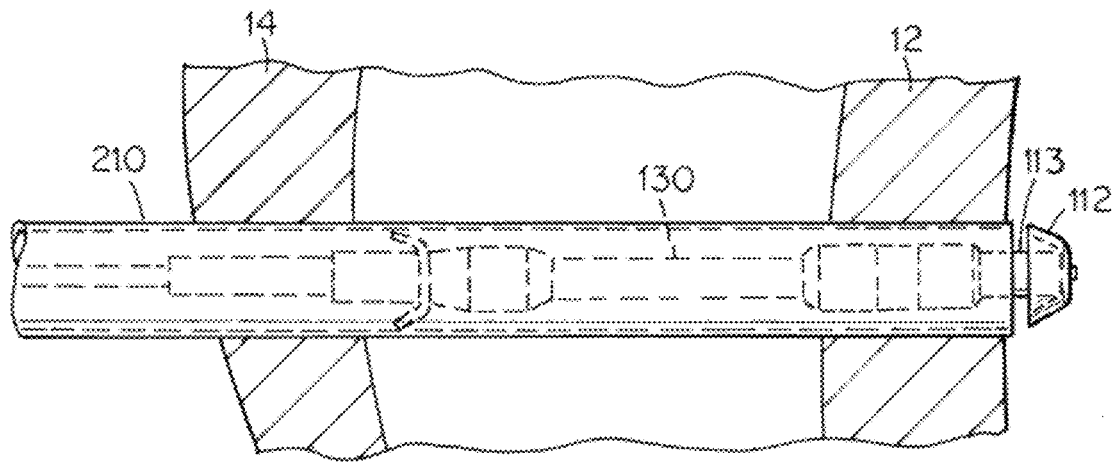
Figure 5C:
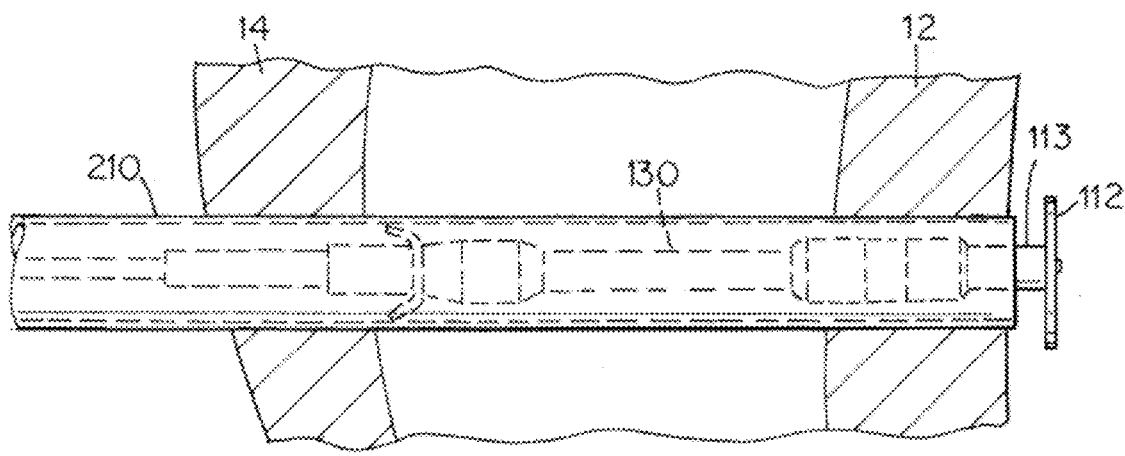
Figure 5D:
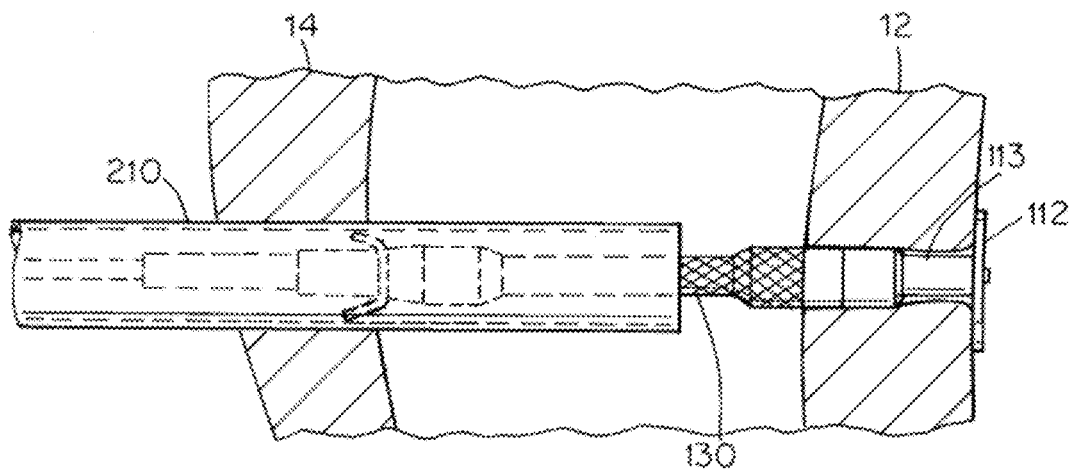
Figure 5E:
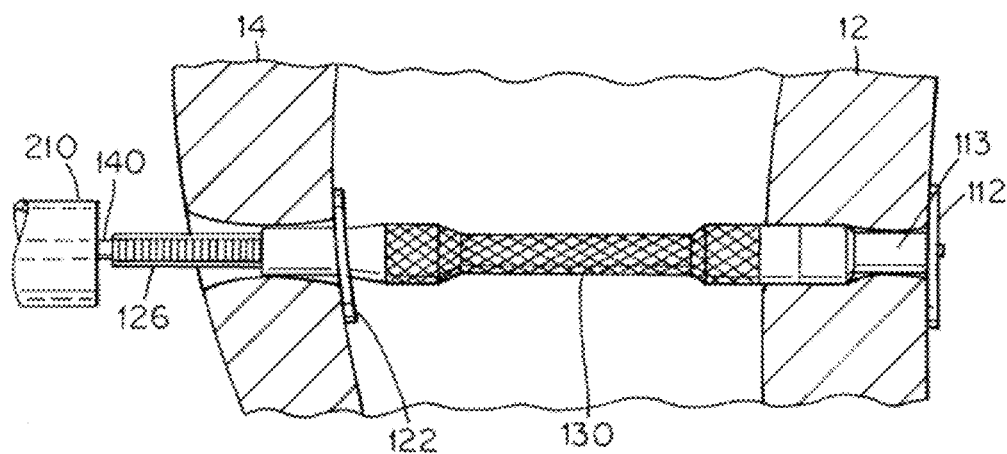

When the distal end of the catheter has reached the space enclosed by the left ventricle, as shown in FIGS. 5B-5C, the first, distal, anchor 110 having a distal anchoring flange 112 is extended outward in a radial direction from a delivery tube 113 of the device so as to from an anchor against the wall of the septum on the side facing the interior of the left ventricle. Subsequently, or at the same time, as shown in FIGS. 5D-5E, the catheter housing 210 may be drawn back toward the point of entry so as to expose the mechanical assist device 100 within the left ventricle, adjacent the ventricular septum, along with other components of the device.

Figure 5F:
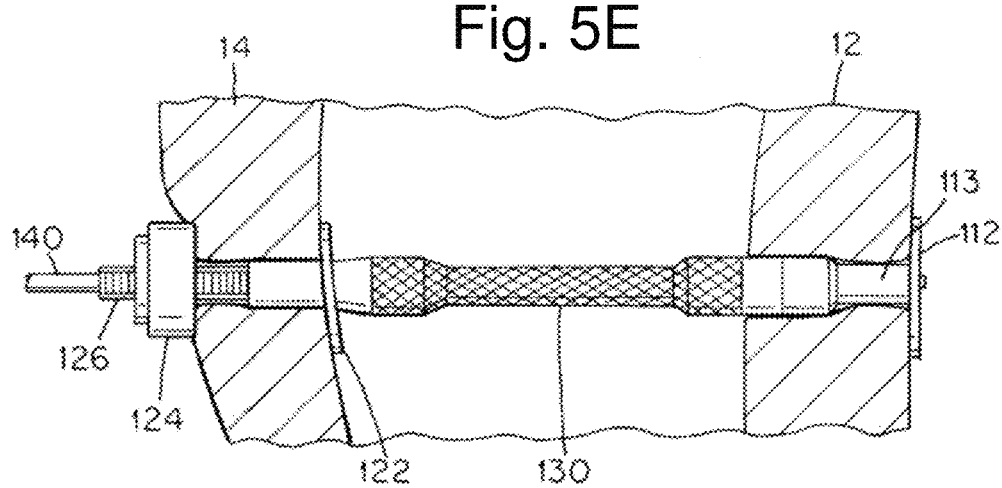

Once the catheter housing 210 is suitably withdrawn and removed from the device, the second, proximal, anchor may be suitably deployed. For example, as shown in FIG. 5E, an optional proximal flange 122 is extended radially outward so as to reside against the inner wall of the right ventricle. As shown in FIG. 5F, a first fastening component 124 (e.g., anchoring cap) is slid, twisted, or ratcheted on to the second fastening component 126 (e.g., track), opposite the flange 122, so as to sandwich the right ventricular free wall 14 therebetween. As a result, the device is firmly secured to both the ventricular septum 12 and the right ventricular free wall 14. Accordingly, during use, the ventricular septum 12 and the right ventricular free wall 14 are forced to move back and forth relative to one another according to contraction and extension motion of the actuator 130.

As discussed herein, in certain embodiments, where the device is implanted within a chamber of the heart, having been pierced through by the sharp distal end of the catheter, respective openings are formed through opposing tissue walls. As a result, there may be a tendency for fluid to leak or otherwise flow undesirably through the pierced opening(s). Accordingly, the respective anchors, when deployed, may be arranged to form a suitable seal with the tissue wall, so as to prevent leakage through the wall. In some embodiments, the anchor(s) may be combined with another material, such as a sealant material or suture. For instance, when an anchor is appropriately engaged at a tissue wall, a sealant material may be applied to the opening, so as to obstruct fluid flow therethrough. Or, a suture arrangement, such as a purse string suture, as discussed above, may be used to effectively close the opening.

Implantation of the device may be reversible. For example, once deployed, the device may be removed in a suitable, non-destructive manner. Accordingly, the device may be removed so as to be replaced by another mechanical assist device, or it may be determined that the device is simply no longer needed. In some embodiments, the first fastening component 124 may be removed or disengaged from the second fastening component 126, for example, the first fastening component 124 may be twisted, slid or ratcheted off, in an appropriate manner, from the second fastening component 126. The flanges 112, 122 may be retracted or deflated back, for example, into the delivery tube from where they were initially stored.

Accordingly, for some embodiments, implantation of the mechanical assist device may be temporary (e.g., hours, days, weeks). That is, in some cases, the device may be employed for a period of time, for example, as a post-surgery recovery measure until the heart or other organ suitably recuperates from its previous condition. Though, it can also be appreciated that mechanical assist devices described herein may be used as a permanent implant as well.

In some embodiments, the device may provide a patch for closing a ventricular septal defect during the time when the device is implanted and/or when the device is removed, to obstruct undesirable flow through the defect. For example, where an opening, or defect, already exists in the ventricular wall, during delivery, the ventricular septum need not be punctured. That is, the distal anchor of the device may be delivered directly through the defect and the distal anchor may be deployed on the opposite side of the wall, within the volume of the left ventricle.

When the device is removed, a portion of the distal anchor may be left behind so as to keep the defect closed. In some embodiments, upon implantation and subsequent removal of the device, the distal anchor may be disconnected from the actuator of the device and may remain at the site of the defect. In some cases, an additional patch may be delivered along with the distal anchor so as to sandwich the defect therebetween. For example, upon removal of the device, the distal anchor (located on the left ventricle side) and the additional patch (located on the right ventricle side) may remain to form a suitable closure, obstructing leakage through the defect.

While a sandwich-type closure may be used to close the defect, in some embodiments, a single patch material may be delivered to the defect and may be sufficient to form a suitable defect closure. The distal anchor itself may function as a single patch material, or a separate article may function as a single patch material, allowing for the distal anchor itself to be removed therefrom.

The distal anchor and/or additional patch may be constructed in an appropriate manner. For example, the distal anchor and/or additional patch may be self-expandable, inflatable or may otherwise alter in conformation so as to be able to form an appropriate seal for the ventricular septal defect. Suitable coatings and/or sealants may also be employed with the patch, as appropriate.

The mechanical assist device shown in FIG. 3 was tested, as described below. The device was mounted and tested on a rig having two elastomer sidewalls mounted on an acrylic frame, designed to simulate a heart ventricle. The elastomeric sidewalls were made of a soft silicone rubber having material properties similar to that of living heart tissue. The sidewalls were molded to have different thicknesses to mimic the varying thicknesses of the ventricular septum and right ventricular free wall. In this example, the ventricular septum was simulated using a 10 mm thick sidewall and the right ventricular free wall was simulated using a 5 mm thick sidewall. The mechanical assist device was secured to the opposing sidewalls and the fluid line was connected to a regulated air supply, for actuation thereof.

Figure 6:
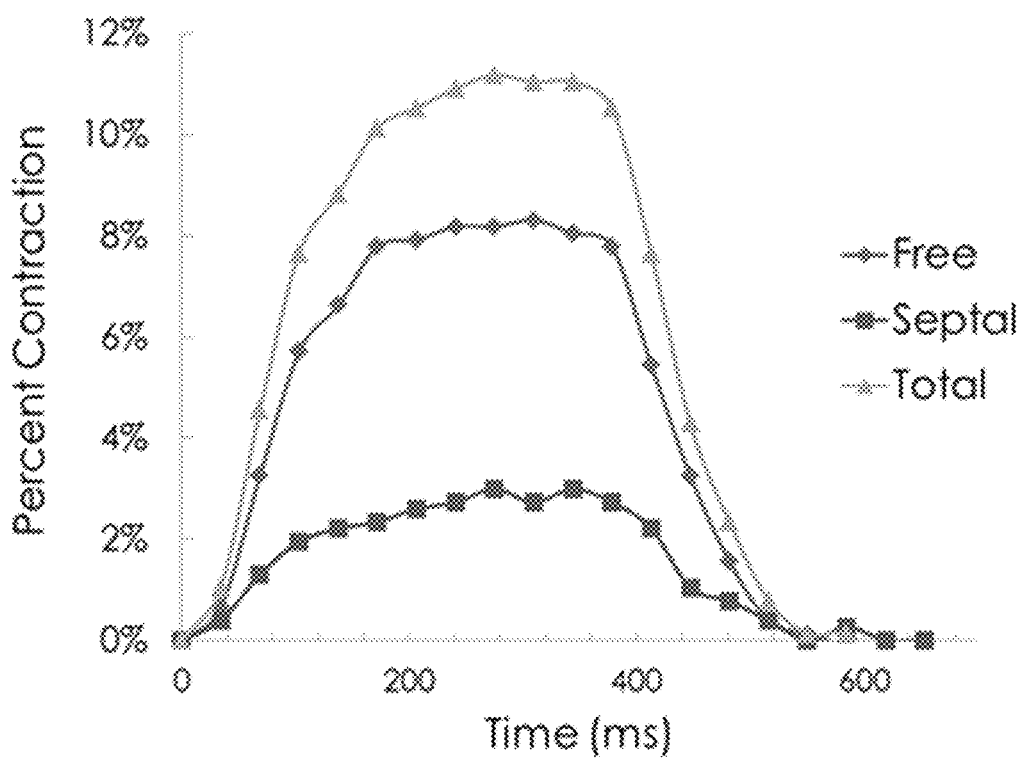
FIG. 6 shows a graph depicting contraction of a mechanical assist device in accordance with some embodiments.

FIG. 6 provides a graph that shows the percent contraction of the mechanical assist device during a cardiac cycle, as tested above. The percent contraction is given by the contracted length of the device as compared to the original extended length, as determined through distance measurements taken at the 10 mm septal wall (simulated ventricular septum) and the 5 mm free wall (simulated right ventricular free wall).

As shown in FIG. 6, the total maximum percent contraction of this particular example during a single cardiac cycle was approximately 11%. Though, it can be appreciated that the percent contraction of various embodiments of the present disclosure may suitably vary. In some embodiments, the percent contraction of the mechanical assist device may be greater than 5%, greater than 10%, greater than 15%, greater than 20%, greater than 25%, or greater than 30%. In some embodiments, the percent contraction of the mechanical assist device may be less than 50%, less than 45%, less than 40%, less than 35%, less than 30%, less than 25%, less than 20%, or less than 15%. Or, the percent contraction of the mechanical assist device may fall within ranges defined by any of the above noted end points. Further, the percent contraction of the mechanical assist device may lie outside of the above noted ranges.

FIG. 6 further shows that the free wall exhibits comparatively more movement as compared to the septal wall, about twice as much, which is within desired parameters for operation of the device within the right ventricle. Accordingly, during use within a right ventricle, it may be desirable for the right ventricular free wall to exhibit a greater degree of contraction as compared to the ventricular septum, so as to push blood toward the right ventricular outflow tract, located opposite the free wall, and adjacent to the septum.

As described herein, movement of the ventricular septum may be determined by movement of the first anchor, and movement of the right ventricular free wall may be determined by movement of the second anchor. Accordingly, in some embodiments, during use, the second anchor, which may function to pull the right ventricular free wall inward, exhibits a greater overall distance of contraction than the first anchor, which may pull the ventricular septum inward. For example, the second anchor may move a distance greater than that of the first anchor by at least 1.5 times, at least 2.0 times, at least 2.5 times, at least 3.0 times, or more. Or, during use, the second anchor moves a greater distance as compared to the first anchor by less than 5.0 times, less than 4.0 times, less than 3.0 times, or less than 2.0 times. In some embodiments, the difference in the amount of contraction between the first and second anchors may fall within ranges defined by any of the above noted end points, or outside of these ranges.

Further, as shown in FIG. 6, the slope of contraction, upon increase, may be steeper than the slope of extension, upon decrease. This is indicative of forced contraction and relatively passive extension of the bladder. Without wishing to be bound by theory, this behavior may be due to the device being actively contracted, where during inflow, fluid is pneumatically pushed into the actuating bladder; and during outflow, fluid is allowed to flow out of the bladder in a more relaxed manner. While, the slope of contraction for the cardiac cycle shown in FIG. 6 is steeper than the slope of extension, it can be appreciated that for certain embodiments, the slope of contraction may be less steep than the slope of extension. For example, the actuator may be configured to have a volume having a negative pressure such that fluid naturally flows into the actuating bladder during contraction while, during extension, the device is configured to more forcefully drawn fluid out from the bladder.

Figure 7A:
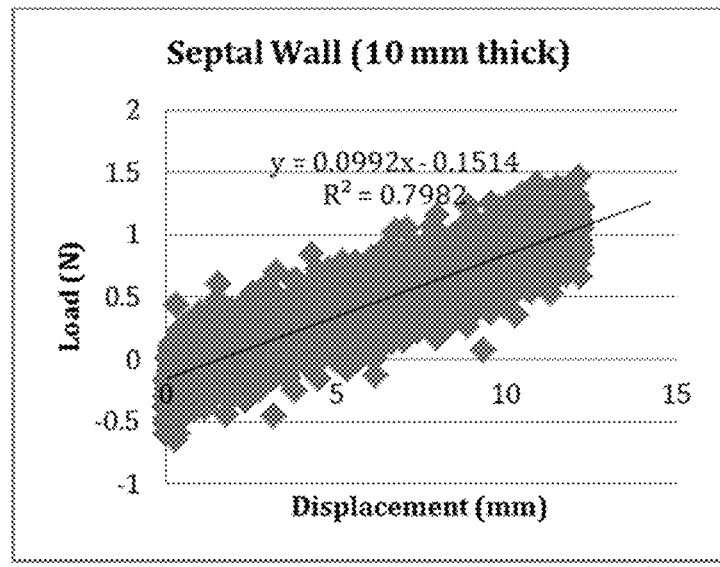
FIGS. 7A-7B show graphs depicting load versus displacement at various regions of a mechanical assist device in accordance with some embodiments.
Figure 7B:
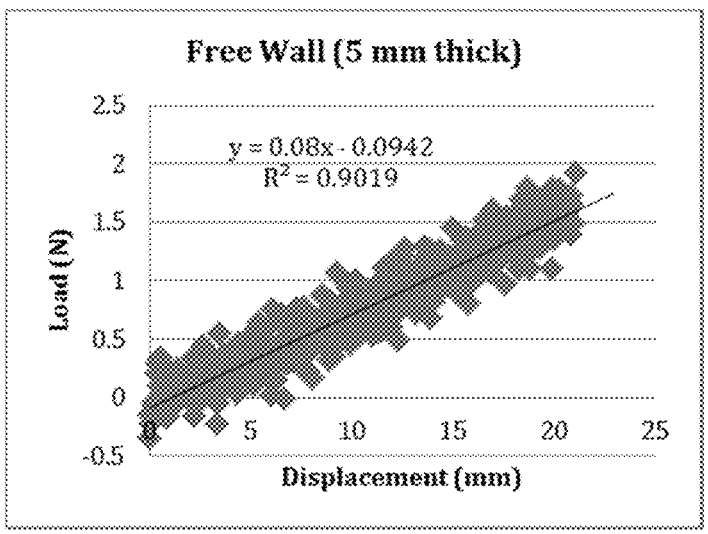

FIGS. 7A-7B depict graphs that show load versus displacement behavior of the mechanical assist device of FIG. 3, as tested above. As shown, the force required to move the septal wall for a particular displacement is generally greater than the force required to move the free wall over the same distance. This observation is expected, given that the thickness of the septal wall is greater than the thickness of the free wall, and so the thicker septal wall would provide a greater degree of resistance to actuation than the comparatively thinner free wall.

Depending on how the mechanical assist device is fabricated, the device may generate any appropriate measure of assistive pressure to the organ within which it is implanted. In some embodiments, the mechanical assist device may generate an additional fluid flow pressure of at least 10 mm Hg, at least 20 mm Hg, at least 30 mm Hg, or at least 40 mm Hg to the organ. Or, the mechanical assist device may generate an additional fluid flow pressure of less than 80 mm Hg, less than 70 mm Hg, less than 60 mm Hg, less than 50 mm Hg, or less than 40 mm Hg to the organ. Or, the added fluid flow pressure generated by the mechanical assist device may fall within ranges defined by any of the above noted end points, or outside of the above noted ranges.

Devices in accordance with the present disclosure may be used for a variety of medical applications. For example, mechanical assist devices described herein may be implanted in any suitable enclosed space of any appropriate organ, such as the heart as described above, including the right ventricle, left ventricle, right atrium, or left atrium. However, it should be appreciated that the device may be implanted to mechanically assist other organs such as the urinary bladder, colon, stomach, or other organs whose function may benefit from contractile assistance. Mechanical assist devices described herein may also be suitably sized, with appropriate materials, for people and animals of varying ages, for example, adults, children, elderly, etc.

During use, operation of the mechanical assist device may be appropriately monitored. That is, a number sensors may be employed at various locations to sense real-time information about the heart and/or the device itself. Based on the sensed parameters, certain parameters of the device may be suitably adjusted. For example, the actuator may be configured to contract and extend, with appropriate timing and force, according to the demands of the heart.

In some embodiments, a pressure/flow sensing and mechanical failure sensing system may be provided. Such a system may employ a series of thermal, optical, and mechanical sensors distributed around the device so as to provide real-time flow and pressure readings. For example, the pressure within the actuating bladder, volume and flow rate in and out of the actuating bladder may be continuously or intermittently monitored during use.

In some embodiments, the actuating fluid may exhibit radioopacity so that suitable imaging may occur. Such imaging may allow a user to track contraction and extension movements of the device.

When the heart is monitored, leads may be placed at appropriate locations of the heart so as to provide pertinent electrocardiogram information regarding the cardiac cycle. The cardiac cycle refers events related to the flow of blood in and around the heart from the beginning of one heartbeat to the beginning of the next. The cardiac cycle is coordinated by a series of electrical impulses produced by heart cells located at various nodes of the heart, which results in motion of the heart through the different stages of the cardiac cycle.

In the first stage of the cardiac cycle, termed, "early diastole," the semilunar valves (pulmonary and aortic valves) close, the atrioventricular valves (mitral and tricuspid valves) open, and the heart is in a relaxed state. The second stage is "atrial systole," which is when the atrium contracts, causing blood to flow from the atrium to the ventricle. The third stage is "isovolumic contraction," which is when the atrioventricular and semilunar valves close and the ventricles begin to contract. In the fourth stage, "ventricular ejection," the semilunar valves are open and the ventricles are contracting and emptying through the semilunar valves. In the fifth stage, "isovolumic relaxation time," the semilunar valves close and the ventricles end their contraction.

Electrical, mechanical and other pertinent information recorded by the sensors located at various nodes of the heart and around the mechanical assist device may be sent as feedback to a controller to provide an indication of the particular cardiac cycle stage(s) of the heart and/or the status of the device. The controller may include a processor that interfaces with the various sensors, power source(s), fluid pump(s) and various aspects of the mechanical assist device (including anchors and actuator) so as to control the timing and force under which the device is actuated. With this information, the controller may synchronize the device to match the pattern of observed or recorded electrocardiogram information, so as to assist contraction of the organ in a natural manner.

Accordingly, the device may be configured to contract when the electrocardiogram indicates that the chamber within which the device is implanted is scheduled to contract, so as to suitably assist ejection of blood from the chamber. For example, when it is determined that the chamber will or should undergo natural contraction, pressurized fluid may be forced into the actuating bladder via the fluid line, so that the device actuates along with the natural contraction motion of the chamber. Further, in between contractions, when the chamber naturally relaxes, the fluid within the actuating bladder may be caused to flow back out through the fluid line, allowing the actuating bladder to extend into a relaxed state.

Aspects of the present disclosure may employ various communication tools for providing feedback and sensed information, so as to manipulate various operational parameters as appropriate. For example, sensed information (e.g., electrocardiogram data) may be provided to a controller via cable, wireless and/or Bluetooth communications protocols, etc. Further, a suitable graphic user interface may enable a user or distributor of the device to re-configure and/or adjust various parameters of the device, as desired.

Mechanical assist devices in accordance with the present disclosure may be fabricated by any suitable method, using appropriate materials. FIGS. 8A-8G depict an embodiment where a mechanical assist device is fabricated. In each figure, a schematic of the device is shown in the drawing above, and a photo of the device is shown below.

Figure 8A:
FIGS. 8A-8G show fabrication of a mechanical assist device in accordance with some embodiments.
Figure 8B:
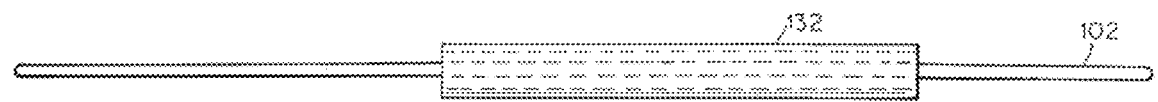

FIG. 8A shows a support rod 102 made from a suitable material (e.g., metal, plastic, etc.). In FIG. 8B, a membrane 132 is placed over the support rod. The membrane 132 may be a pre-molded elastomeric material (e.g., silicone-based polymer, ELASTOSIL®, etc.), or any other suitable composition, for example, formed as an inner tubing. The membrane 132 is provided as the material that forms an actuating bladder which may be inflated or distended depending on whether fluid is received therein.

While the membrane 132 may have any suitable thickness, the thickness may be adjusted so as to balance various factors. For example, a thicker membrane may be more robust, i.e., less likely to rupture upon inflation under pressure, yet may require a greater amount of pressure to inflate than a comparatively thinner membrane. While a comparatively thinner membrane may not need as much force to actuate (through inflation), a thinner membrane may have a tendency to be more fragile.

Figure 8C:
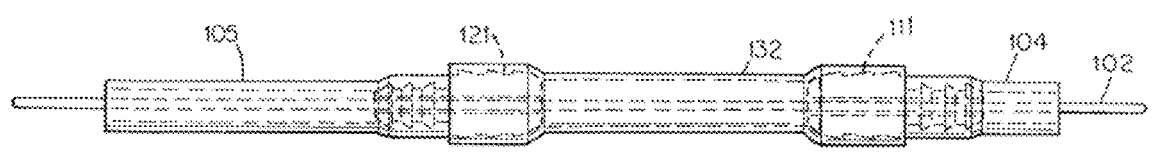

In FIG. 8C, hollow connectors 111, 121 are placed on either side of the support rod 102 such that the membrane 132 fits over the hollow connectors 111, 121. These hollow connectors 121 may be relatively rigid, for example, plastic hollow barbed connectors, so that the opposing ends of the membrane 132 can be flexed tightly over the connectors located on either side. A suitable seal may be formed at the interface between the membrane and the connectors, so as to prevent leakage at the interface. The hollow connectors may be formed of or coated with any suitable material, for example, a polymer (e.g., silicone, polydimethylsiloxane, polyester, etc.) which has a relatively soft surface that allows for the flexible membrane to be secured therewith.

The hollow connectors 111, 121 form the ends of the actuator 130 and the membrane 132 provides the material for forming the bladder within which actuating fluid may flow. Further, fluid connectors 104, 105 are attached to each respective hollow connector 111, 121 on either side opposite where the membrane 132 is located. The fluid connectors 104, 105 are provided for support and housing for the fluid line 140 that provides fluid to the actuator 130 therethrough. In some embodiments (not shown), the fluid connectors may incorporate a valve arrangement, for regulating fluid flow between the fluid line and the bladder.

Figure 8D:
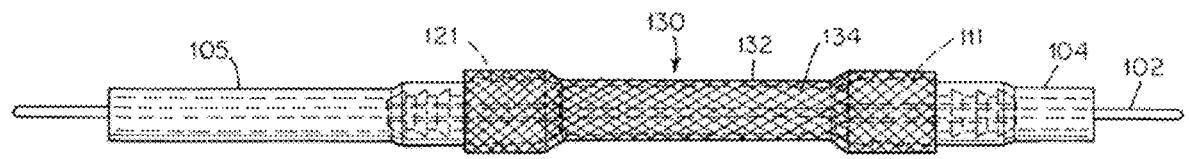

In FIG. 8D, a suitable mesh 134 is placed over the membrane 132 and attached at the hollow connectors 111, 121, forming the actuator 130. In this example, the mesh 134 is designed so as to guide the bladder formed by the membrane 132 in an appropriate manner. That is, as discussed above, when a sufficient amount of fluid, pressurized to a suitable degree, flows into the bladder, the mesh 134 guides expansion of the bladder to contract along its longitudinal axis, and to expand radially.

At this point during fabrication, the actuator 130 is formed, and the anchors are provided next. Though, it can be appreciated that any of the components of the mechanical assist device may be formed in any suitable order.

Figure 8E:
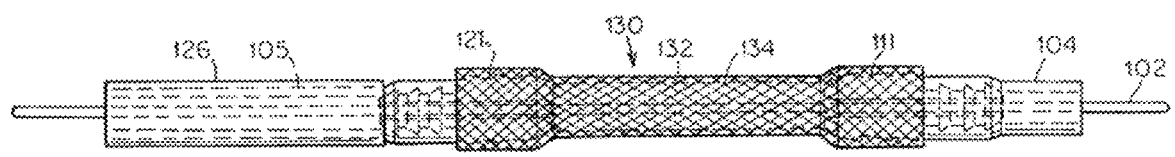
Figure 8F:
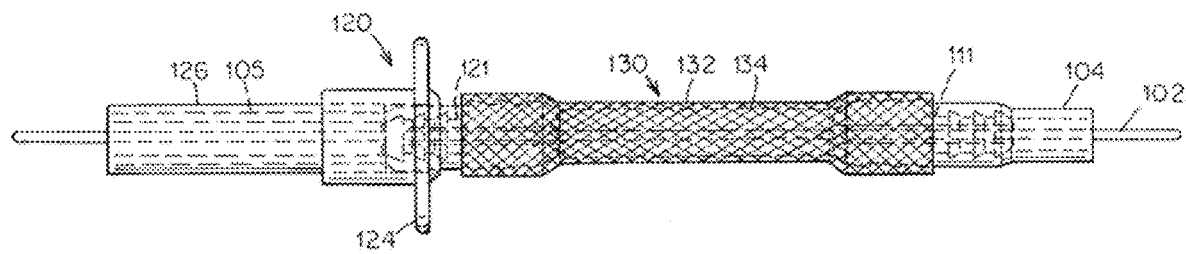

In FIG. 8E, a fastening component 126 is provided on one side of the device, fitted over the fluid connector 105. As further shown in FIG. 8F, the fastening component 126 provides a manner in which another fastening component 124 may be suitably placed and adjusted thereon so as to form an anchor 120. The fastening components may have surfaces (e.g., threads, ratchet/pawl arrangements, etc.) that are complementary to one another. In some embodiments, the a fastening component 124 is screwed, slid or ratcheted on to an appropriate second fastening component 126. Or, in certain embodiments, the first fastening component 124 is molded directly on to or with the second fastening component 126.

Figure 8G:
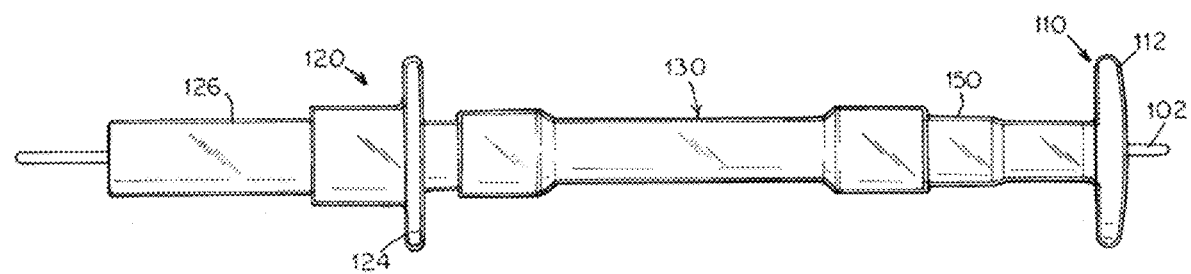

In FIG. 8G, on an opposite side of the device, another anchor 110 is formed. The anchor 110 includes a flange 112 formed over the fluid connector 104. As discussed above, the flange 112 may include any suitable material and may be deployed via any suitable mechanism. In some embodiments, the flange 112 includes an elastomeric material, or any other suitable composition. Or, in certain embodiments, the flange 112 may be extendable and retractable, for delivery and removal of the anchor from the tissue wall.

FIG. 8G depicts an optional outer coating 150 disposed over the anchors 110, 120 and the actuator 130. In some embodiments, the coating 150 may serve to hold the various components of the device together. In some embodiments, the coating 150 may provide a seal around the device to obstruct leakage of any fluid(s) therefrom.

It can be appreciated that embodiments of mechanical assist devices in accordance with the present disclosure may be fabricated in any suitable manner, and may have components arranged in a number of different ways. Below are various embodiments of such devices, which are not meant to limit the scope of the present disclosure.

Figure 9A:
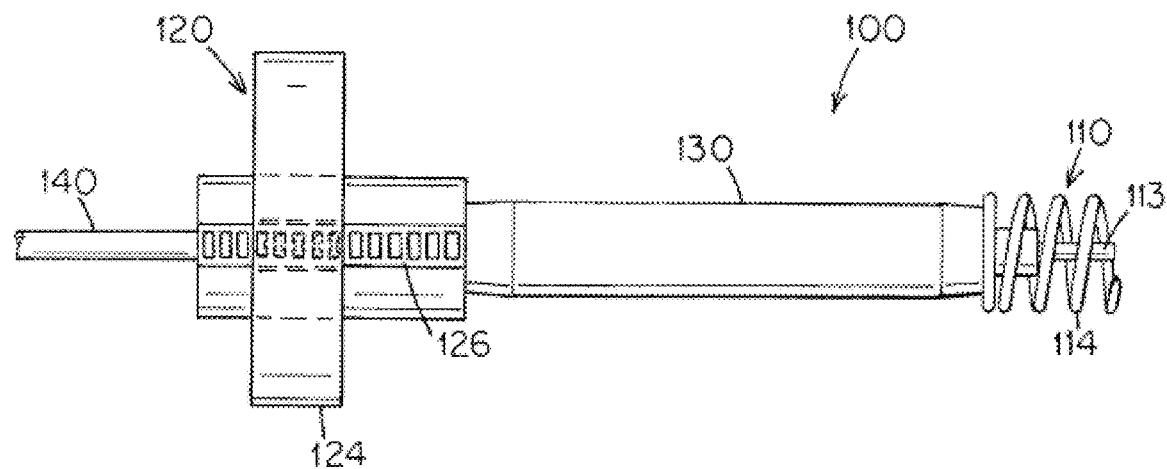
FIGS. 9A-9B illustrate another mechanical assist device in accordance with some embodiments.
Figure 9B:
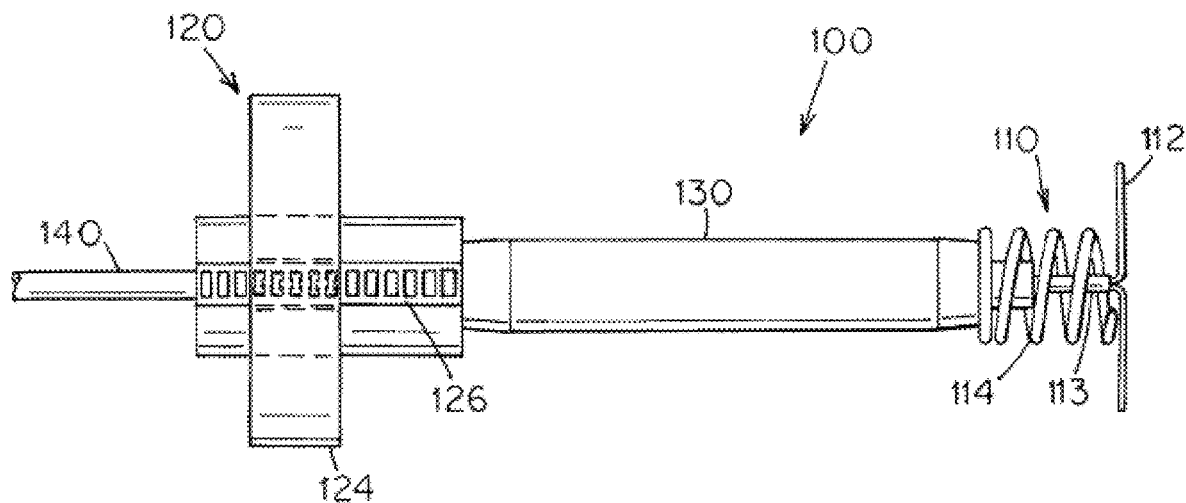

FIGS. 9A-9B illustrate a mechanical assist device 100 having first and second anchors 110, 120 and an actuator 130 coupled therebetween. The first anchor 110 has a delivery tube 113 from which a flange 112 may be stored prior to implantation, as shown in FIG. 9A. Though, when the device is implanted, as shown in FIG. 9B, the flange 112 may be extended from the delivery tube 113 into a deployed configuration.

In addition, the first anchor 110 includes a coring member 114 which, during implantation, may be rotated so as to penetrate into the tissue wall, forming an opening through which the distal end of the device may enter. Once the distal end of the device has suitably penetrated through the tissue wall, the flange 112 may be extended from the delivery tube 113, engaging the anchor 110 with the tissue wall, as discussed above.

The second anchor 120 includes a first fastening component 124 and second fastening component 126, in accordance with various embodiments described herein. Once the first anchor 110 is suitably engaged with a tissue wall at the distal end of the device, the first and second fastening components 124, 126 of the second anchor 120 may appropriately engage with an opposing tissue wall at the proximal end. In this example, the first fastening component 124 ratchets or slides on to the second fastening component 126 and, where desired, is kept in place to hold the device against the tissue wall.

FIGS. 10A-10B provide various embodiments of the first anchor 110, which are similar to that shown in FIGS. 9A-9B, with slight variations. For example, the flange 112 includes a number of members that extend radially outward from the delivery tube 113. In FIG. 10A, the flange 112 includes a number of rods that are initially stored within the delivery tube 113. For instance, the rods may be shape-memory rods (e.g., including nitinol). In some embodiments, the delivery tube 113 provides a shaft through which the rods may be initially stored and subsequently deployed upon suitable engagement with the tissue wall. For example, once the wall is suitably cored therethrough, the flange including rod-like members may be placed in a deployed configuration. In some cases, a support component 115 may be further provided so as to hold the flange 112, delivery tube 113 and coring member 114 appropriately in place. In FIG. 10B, the flange 112 includes a number of petals. As shown in both FIGS. 10A-10B, upon deployment, the members of the flange 112 (e.g., rods, petals, etc.) extend outwardly from the delivery tube 113 and form a configuration that is radially outward in a direction substantially perpendicular to the delivery tube 113, so as to resist withdrawal of the device from the tissue wall.

Figure 11:
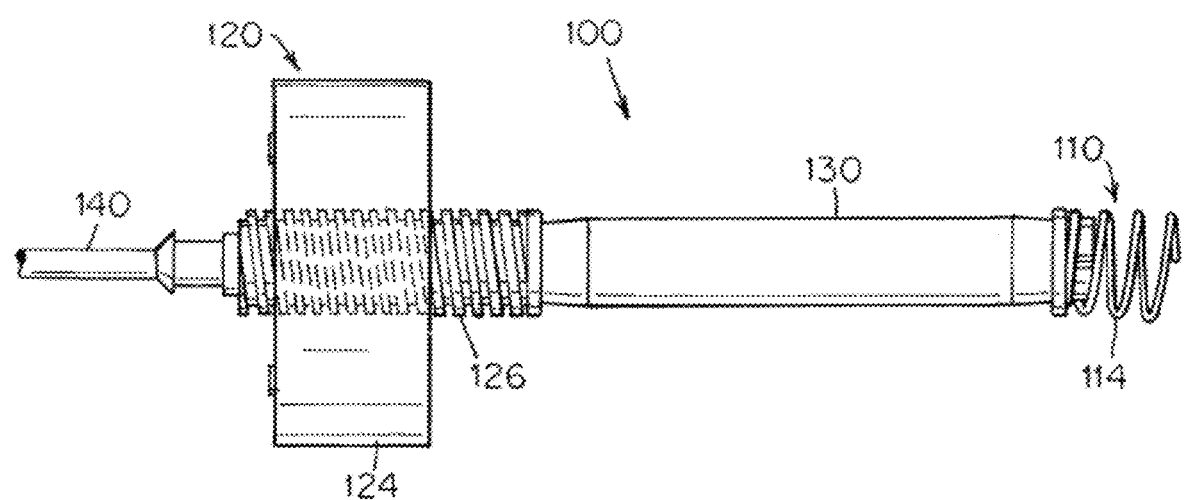
FIG. 11 shows another mechanical assist device in accordance with some embodiments.

FIG. 11 depicts another embodiment of a mechanical assist device 100 having first and second anchors 110, 120 and an actuator 130. The first anchor 110 has a coring member 114 that, as discussed above, may be rotated in a manner that creates an opening through the tissue wall. The second anchor 120 includes first and second fastening components 124, 126, in accordance with various embodiments described herein. In this example, the first and second fastening components 124, 126 have threaded surfaces that are complementary to one another. Accordingly, the first fastening component 124 (threaded nut) may be screwed on to the second fastening component 126 (hollow threaded bolt) and stays in place at the appropriate location so as to hold the device against the tissue wall.

Figure 12A:
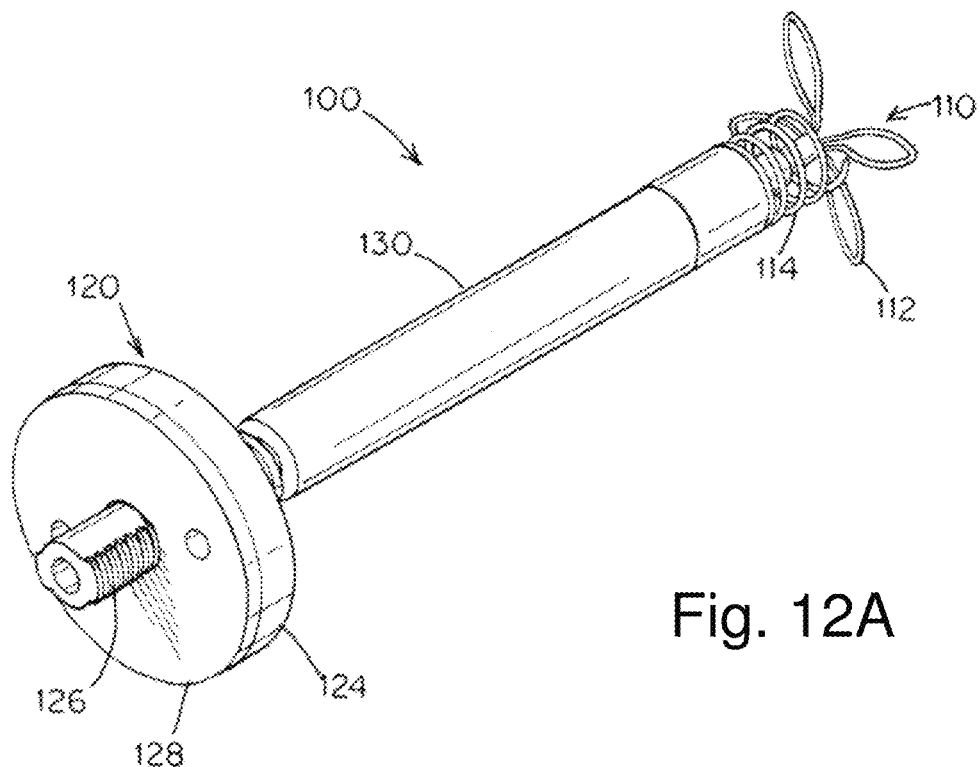
FIGS. 12A-12B depict a mechanical assist device in extended and contracted states in accordance with some embodiments.
Figure 12B:
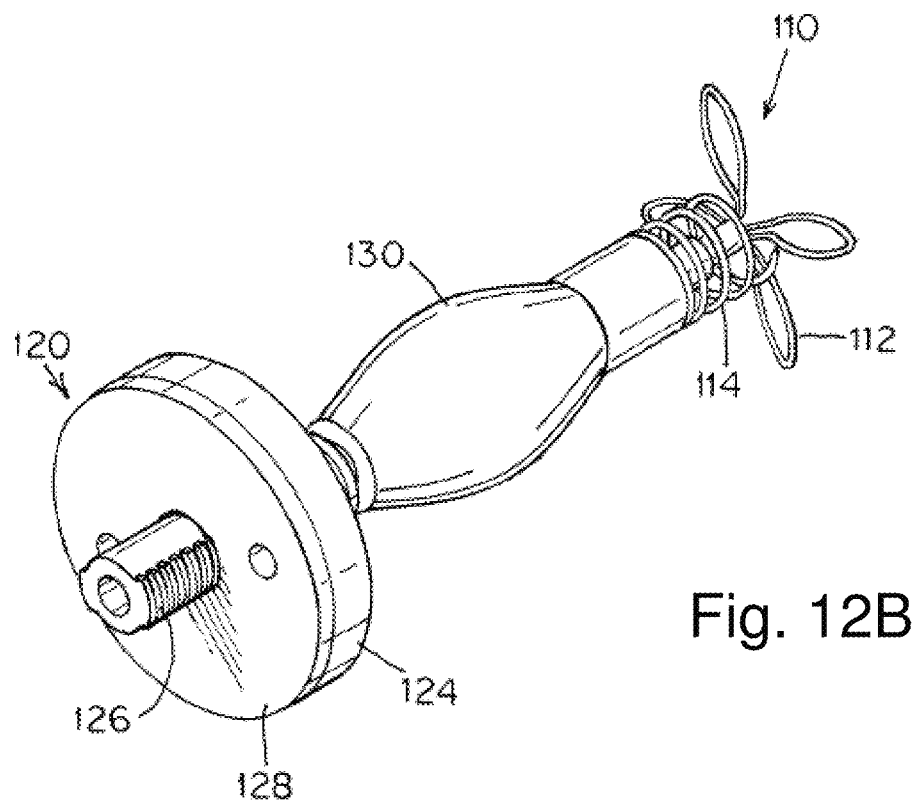

FIGS. 12A-12B depict another embodiment of a mechanical assist device 100 including anchors 110, 120 disposed on either side of an actuator 130. The first anchor 110 has a coring member 114 similar to that shown above with respect to FIG. 10B. Here, the flange 112 of the first anchor 110 is shown to be in a deployed configuration, extending outward from the delivery tube. The second anchor 120 includes first and second fastening components 124, 126 secured to one another, as shown and described further in FIGS. 13A-13C. The actuator 130 of FIGS. 12A-12B includes an inner, elastic bladder, which contracts upon inflation. In accordance with embodiments of the present disclosure, a guiding mesh is disposed over the inner bladder. As further described herein, the actuator also includes an outer, elastic coating over the mesh covered bladder, providing a seal for the actuator so that fluid injected therein does not undesirably leak.

Figures 13A, 13B:
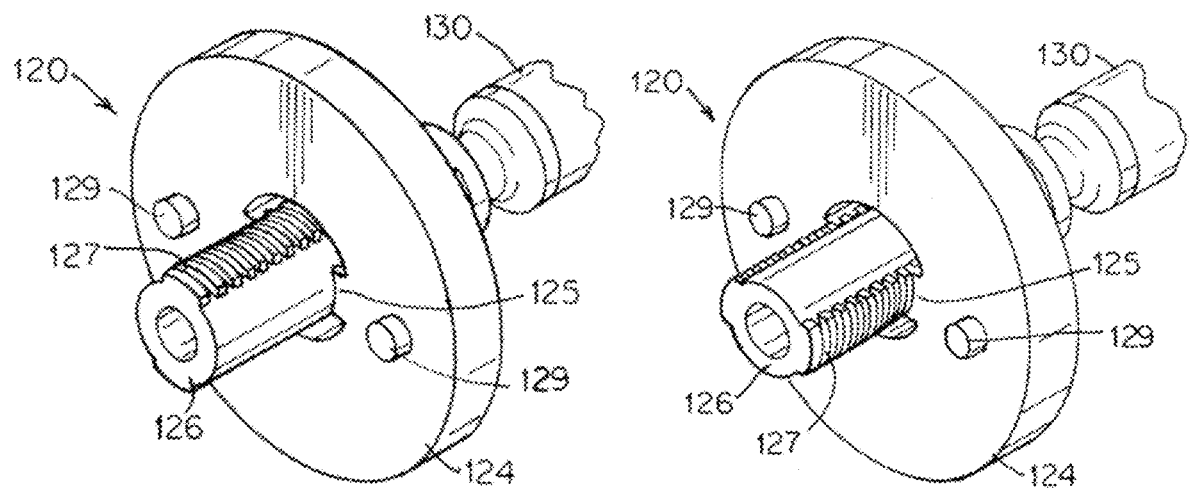
FIGS. 13A-13C show an anchor of a mechanical assist device in accordance with some embodiments.
Figure 13C:
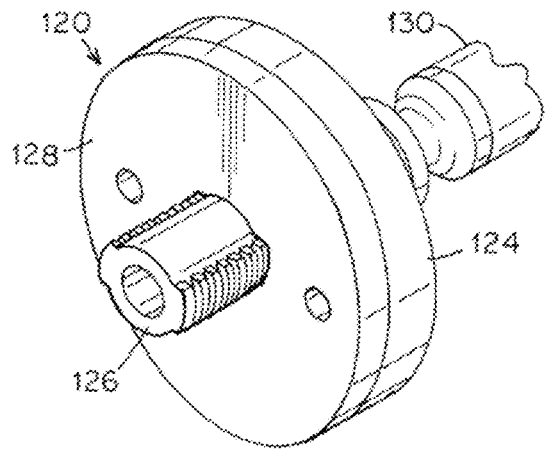

FIGS. 13A-13C show a close-up view of an embodiment of an anchor 120 of a mechanical assist device. In some embodiments, such an anchor may be engaged, upon implantation of the device, at a proximal location (e.g., right ventricular free wall). The anchor 120 includes a first fastening component 124, shown here as a ratcheting nut, and a second fastening component 126, shown as a ratcheting bolt, with respective surfaces 125, 127 that are complementary to one another. The first fastening component 124 has tabs 125 that protrude into the hollow bore of the nut. The second fastening component 126, in turn, includes ridges having slots 127 that are complementary to the tabs 125 of the first fastening component 124, for engaging therewith.

In FIG. 13A, the first fastening component 124 slides on to the second fastening component 126, yet the complementary surfaces 125, 127 of the respective components are not yet engaged. That is, the tabs 125 of the first fastening component 124 are rotatably displaced from the ridges with slots 127 of the second fastening component 126. Accordingly, the first and second fastening components 124, 126 are in an unlocked configuration, able to slide relative to one another along the longitudinal axis of the device, without substantial resistance.

FIG. 13B depicts the first and second fastening components 124, 126 engaged with one another. As shown, the first and second fastening components 124, 126 are rotated with respect to one another such that the tabs 125 of the first fastening component 124 are substantially interdigited with the slots 127 of the second fastening component 126. As a result, in this configuration, the first and second fastening components 124, 126 are prevented from sliding relative to one another along the longitudinal axis of the device. Though, the first and second fastening components 124, 126 may be separated, by first rotating the respective tabs 125 and slots 127 out of engagement.

FIG. 13C shows a securing disc 128 that prevents rotation of the first and second fastening components 124, 126 with respect to one another. As shown, the ratcheting nut includes a pair of protrusions 129 that are sized to fit within respective openings of the securing disc 128. Once the securing disc is fitted over the ratcheting bolt and secured thereto, and further placed against the ratcheting nut such that the protrusions 129 of the nut are inserted within the openings of the securing disc 128, as shown in FIG. 13C, the respective nut and bolt are in a locked configuration. As a result, the anchor 120 may be suitably fixed in place. It can be appreciated that fastening components of anchors of devices in accordance with the present disclosure may be arranged in other configurations than those expressly shown and described, and may be deployed in any suitable manner.

Figure 14:
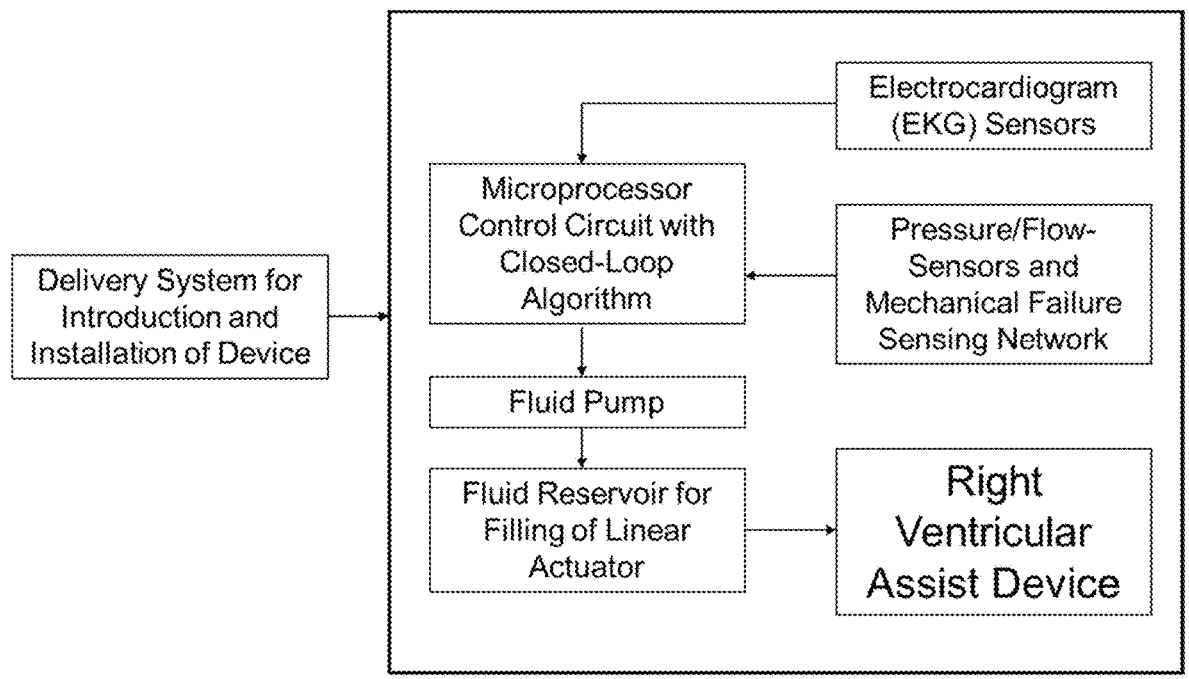
FIG. 14 illustrates a schematic diagram of a system employing a mechanical assist device in accordance with some embodiments.

FIG. 14 illustrates a schematic diagram of an embodiment of a system provided for use with a mechanical assist device. The example of FIG. 14 shows the mechanical assist device to be a right ventricular assist device, however, it can be appreciated that such a system may be employed for any other suitable mechanical assist device. As shown, a delivery system for the introduction and installation of the device in an organ, such as the right ventricle, may be provided. Upon implantation, the device is coupled to a microprocessor control circuit with a closed loop algorithm for controlling actuation of the device. As further shown, to actuate the mechanical assist device, the control circuit actuates a fluid pump, which draws actuating fluid from a fluid reservoir, for filling the actuator, resulting in contraction thereof. Electrocardiogram sensors, pressure/flow sensors and a mechanical failure sensing network are placed at appropriate locations around the organ and the device, so as to provide feedback to the control circuit. Accordingly, based on the feedback information, the control circuit may manage the timing of contraction of the assist device to be synchronized with that of the heart. It can be appreciated that the system of FIG. 14 is provided as an exemplary embodiment, and that suitable variations of the above system for a mechanical assist device may be employed.

It may be preferable for mechanical assist devices according to the present disclosure to be easily and firmly deployed at the site of implantation. That is, for the device to function in a desired manner, the anchors should be suitably installed in a relatively straight-forward minimally invasive manner, with little to no risk of detachment and/or shunting at the tissue wall location. As discussed herein, when embodiments described herein are appropriately implanted and used as a right ventricular assist, the device may be firmly attached at the ventricular septum and the right ventricular free wall. The respective anchors of the device may cover a suitable amount of area such that, during operation, a substantial portion of the ventricular septum and/or right ventricular free wall undergoes contractile motion.

In addition, the device, or a portion thereof, may be structured so as to be easily retrievable from the site of implantation without the occurrence of significant damage to the septum and neighboring structures. For instance, the actuator portion of the device may be removed from the site of implantation, while leaving one or more of the anchors in place. Or, the entire device may be removed from the site of implantation. In some embodiments, when a device, or a portion of the device, is removed, shunting between the ventricles, or other chambers, is minimized or does not occur.

In some embodiments, as discussed further below, the first and/or second anchor has a multiple component construction. For example, the anchor(s) may include a flange and an anchoring member that may be coupled together for securing the device to the appropriate tissue wall, such as by compressively sandwiching the tissue wall on opposing sides. Such arrangements may allow for the anchor(s) to be adjusted to suitably correspond to the particular thickness of the tissue wall. To provide for an increasingly natural pumping action, it may preferable for a substantial portion of the tissue wall (e.g., ventricular septum) to be pushed/pulled back and forth, rather than only a relatively small area of the tissue wall.

The device, or a portion thereof, may be removed and/or replaced without incurring damage to anatomical structures. In various embodiments, such arrangements may provide for relatively simple deployment, in particular, to the ventricular septum, while reducing the potential for damage to the septum and/or other organs. For patients where ventricular support may be preferable for a temporary period of time, the actuating portion of the device may be attached and detached as desired.

For some embodiments, the anchor(s) may include one or more sutures or strings that allow for the flange and the anchoring member to be drawn together in a taut configuration. That is, the strings pull the flange toward the wall while the anchoring member is pushed toward the flange, for coupling therebetween. FIGS. 15A-15E depict an exemplary process of implanting such an anchor across a ventricular septum 12. While the anchor in this example is implanted across a ventricular septum, it can be appreciated that embodiments of the present disclosure may be deployed and used in any suitable tissue wall. In this embodiment, after the appropriate surgical incisions are made to provide access to the heart, a catheter is deployed so as to provide a clear passageway to the septum 12.

Figure 15A:
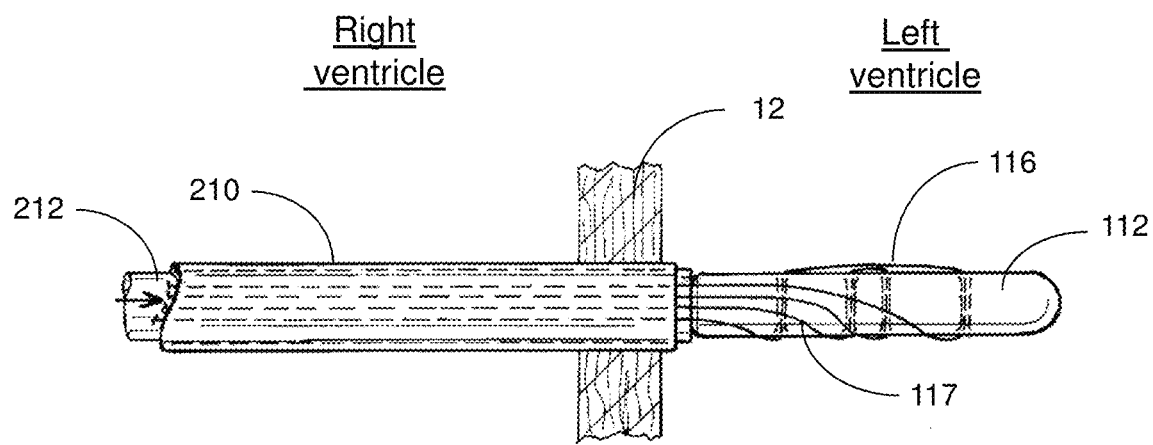
FIGS. 15A-15E depict implantation of another mechanical assist device in accordance with some embodiments.

Upon insertion into the catheter housing 210 (e.g., delivery sheath), as shown in FIG. 15A, a positioning tool 212 is used to push the flange 112 in a distal direction through the housing 210, which extends through the pierced opening of the septum, and tunnels into the left ventricle. It can be appreciated that any appropriate method may be used to deploy the catheter housing, anchor and positioning tool. For example, a 14 Fr sheath may be used under 3D echocardiography guidance.

Figure 15B:
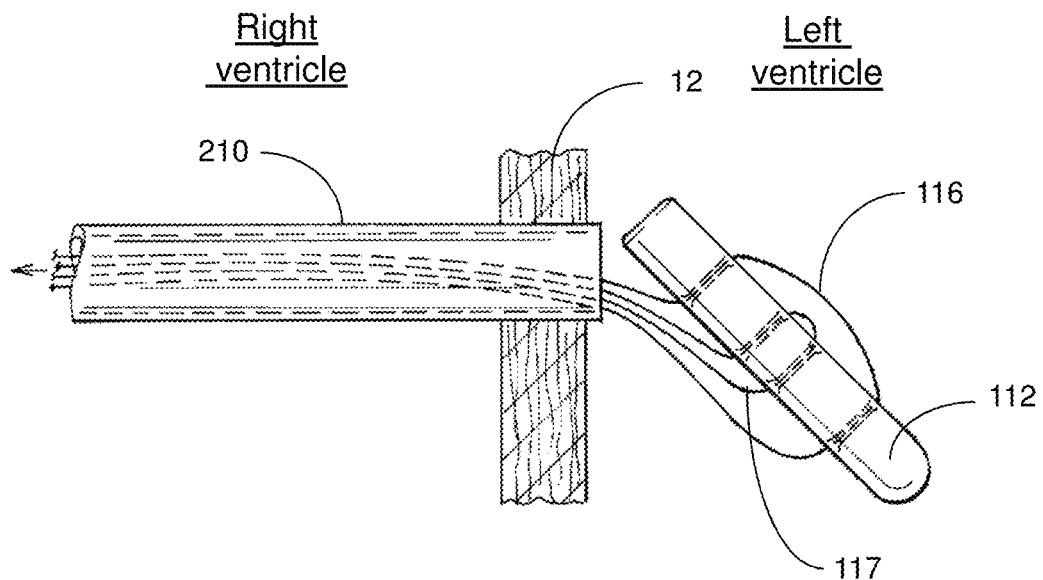

In this embodiment, the flange 112 has a rod-like shape so that it is able to lay or otherwise be oriented in a manner that permits passage through the catheter housing 210. In this embodiment, the flange 112 has holes through which sutures 116, 117 are threaded, allowing for the flange 112 to be manipulated from afar. FIG. 15B shows pulling of the sutures 116, 117 in a proximal direction, resulting in re-orientation of the flange 112 such that the longitudinal axis of the flange 112 begins to align with the ventricular septum 12. Once suitably aligned with the ventricular septum 12, the flange 112 is then generally unable to pass back through the opening.

Figure 15C:
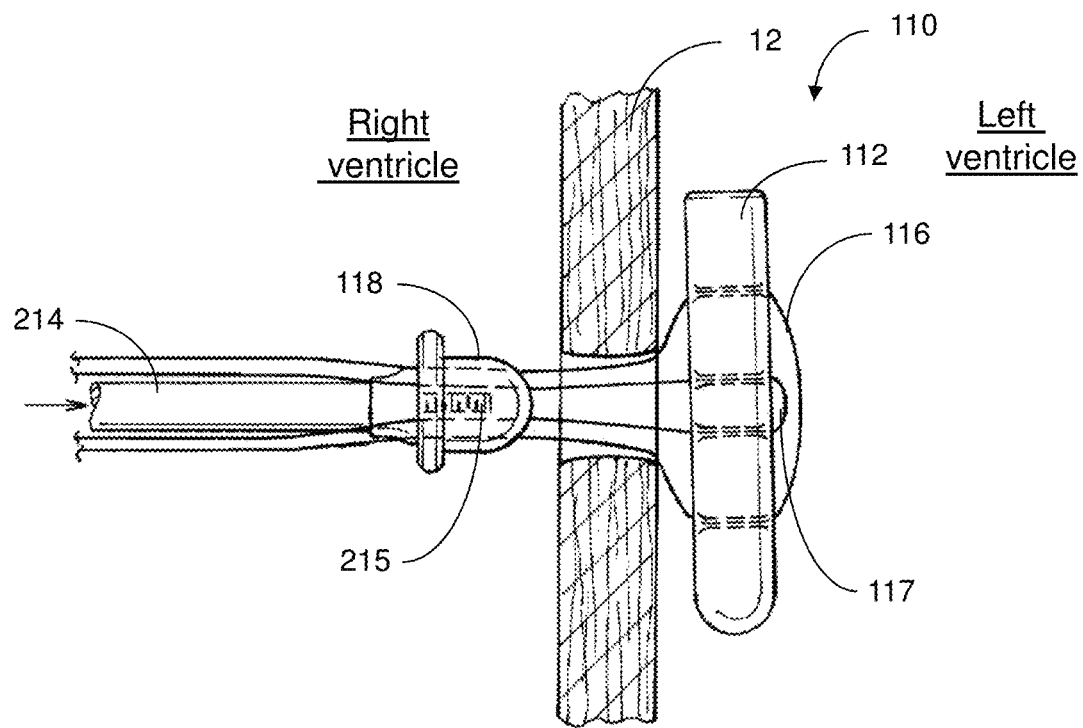

As the sutures 116, 117 are pulled further, as shown in FIG. 15C, the flange 112 ultimately re-aligns so as to reside against the septum. The flange 112 covers a substantial area of the septal wall, so that upon contraction of the overall device, much of the septal wall is actuated back and forth, providing an effective pumping action. This is in contrast to instances where the flange is only able to move a small portion of the septal wall (e.g., when the flange is relatively short/small).

As further depicted, as the flange 112 is pulled against the septal wall, a positioning tool 214 is used to advance an anchoring member 118 toward the flange 112. In this embodiment, the anchoring member 118 is constructed as a plug that is shaped to form a seal with the septum as it is inserted therein. The positioning tool 214 may include a threaded portion 215 that is complementary with a threaded portion on an inner surface of the anchoring member 118, for advancement, retraction or other manipulation of the anchoring member 118.

Figure 15D:
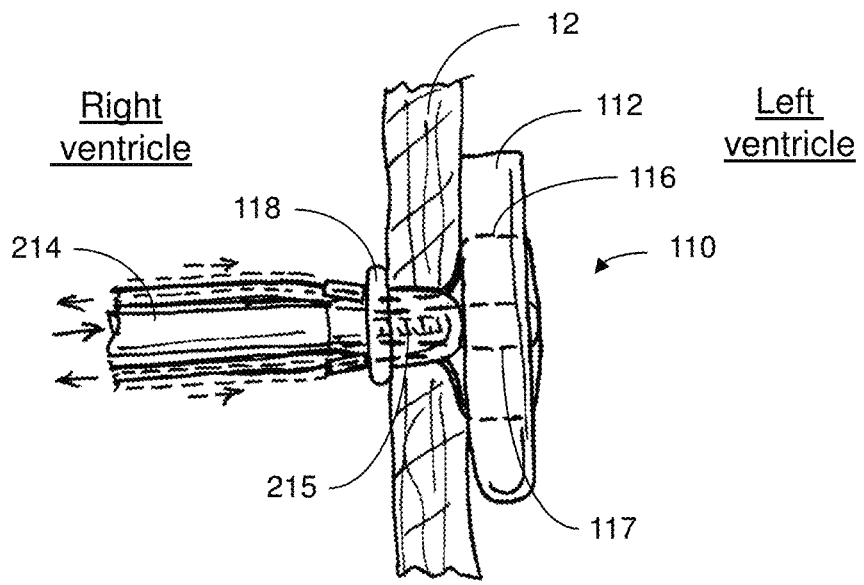
Figure 15E:
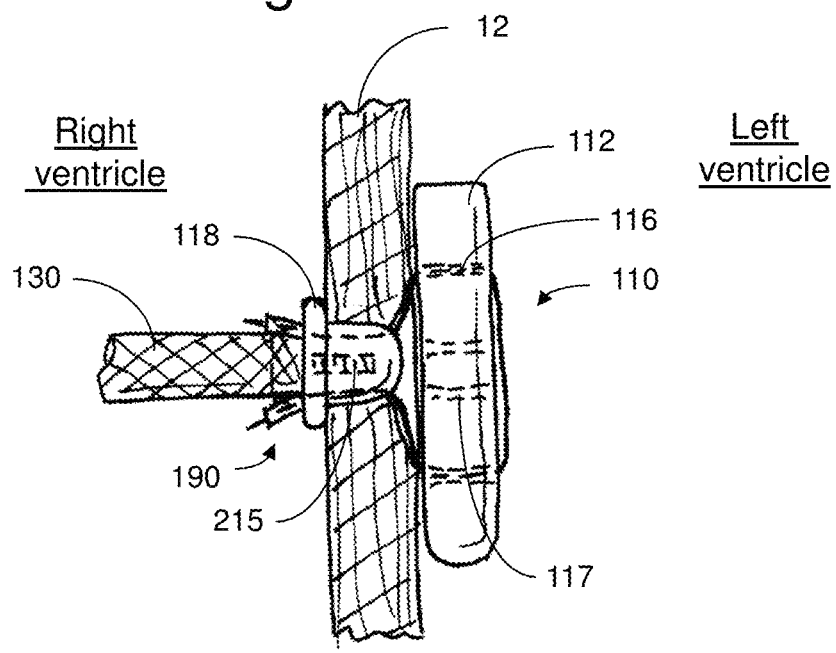

FIG. 15D depicts the process of pulling the sutures 116, 117 toward a proximal direction (as depicted by the solid arrows) and advancing the anchoring member 118 toward a distal direction (as depicted by the dashed arrows), urging the flange 112 and the anchoring member 118 toward one another. When the flange 112 and anchoring member 118 are close enough to compress the ventricular septum 12, so as to form a seal between the left and right ventricles, the sutures are crimped 190, as illustrated in FIG. 15E. Such a seal prevents or otherwise obstructs shunting between ventricles during or after device operation. The tension between the flange and plug is, hence, maintained so as to hold the components in place while preventing or otherwise obstructing fluid flow between the neighboring chambers. The positioning tool 214 may then be removed, for example, by unscrewing the tool from the anchoring member 118.

As further depicted in FIG. 15E, the actuator 130 is then attached or otherwise coupled to the anchor 110, via the anchoring member 118. In this embodiment, after the positioning tool 214 is withdrawn (e.g., unscrewed, decoupled) from the anchoring member 118, the actuator 130 is coupled thereto. As discussed above, upon activation of the actuator 130, the areal coverage of the flange 112 is such that a substantial portion of the septal wall moves along with the actuator, leading to a desirable pumping action, similar to that experienced for normal healthy anatomy. In an example, the flange 112 may have a length of approximately 15 mm, a width of approximately 4.5 mm and a thickness of approximately 1 mm. Though, it can be appreciated that other dimensions are possible.

In this embodiment, the actuator 130 may be easily removed (e.g., unscrewed) from the anchoring member 118. In some cases, the ventricular assist device is intended to be used temporarily. Accordingly, it may be preferable for the actuator 130 to be removed, while leaving the anchoring member 118 and flange 112 in place, maintaining the seal between chambers.

Alternatively, in an embodiment, the anchor(s) may include a flange 112 having folding wings that may be furled during advancement through the catheter housing 210. Once the flange 112 is sufficiently advanced therethrough, the wings are placed in an outstretched position.

Figure 16:
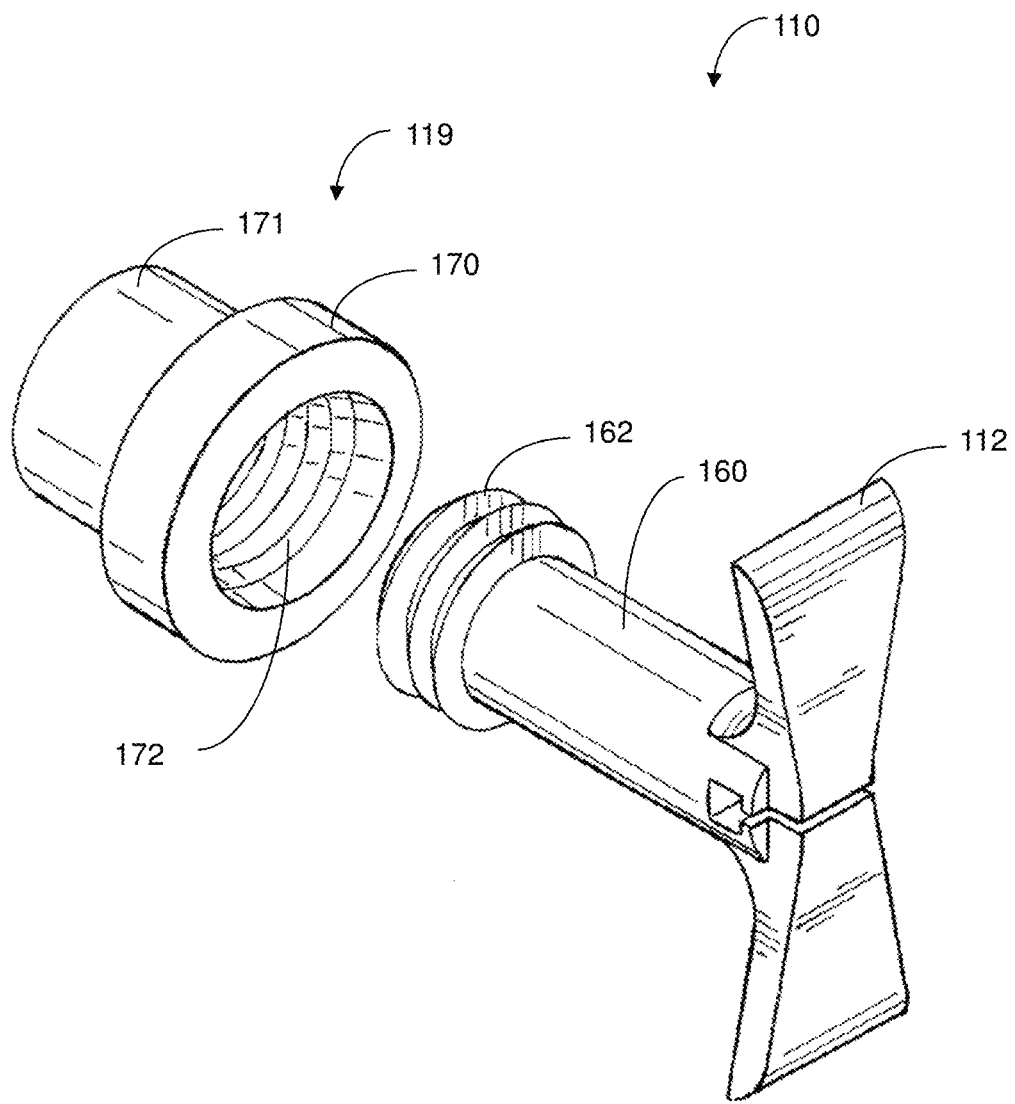
FIG. 16 shows a perspective view of an anchor for use in a mechanical assist device in accordance with some embodiments.

FIG. 16 depicts another two-piece anchor 110 having a flange 112 with wings supported by and extending from a shaft 160. Also extending from the shaft 160 at an end opposite the flange 112 are protruding teeth 162 for locking the anchor in place when coupled with corresponding recesses, described below. The inner surface of the shaft 160 may also include a threaded portion (not expressly shown in FIG. 16), which may be suitably coupled with a complementary positioning tool, for advancement of the shaft/flange in a distal direction, or retraction in a proximal direction, as desired.

The anchor 110 further includes an anchoring member 119 provided as a nut having a distal portion 170 and a proximal portion 171. In this embodiment, the inner surface of the nut includes recesses 172 complementary to the protruding teeth 162, for forming a locking arrangement when coupled together. As discussed further below, the distal portion 170 of the anchoring member 119 may be suitably structured to push up against the ventricular septum 12 to form a seal on the right ventricle side of the septal wall. The proximal portion 171 of the anchoring member 119 may be slightly smaller in width/diameter, to allow for a positioning sheath to push the anchoring member 119 forward when desired.

Figure 17A:
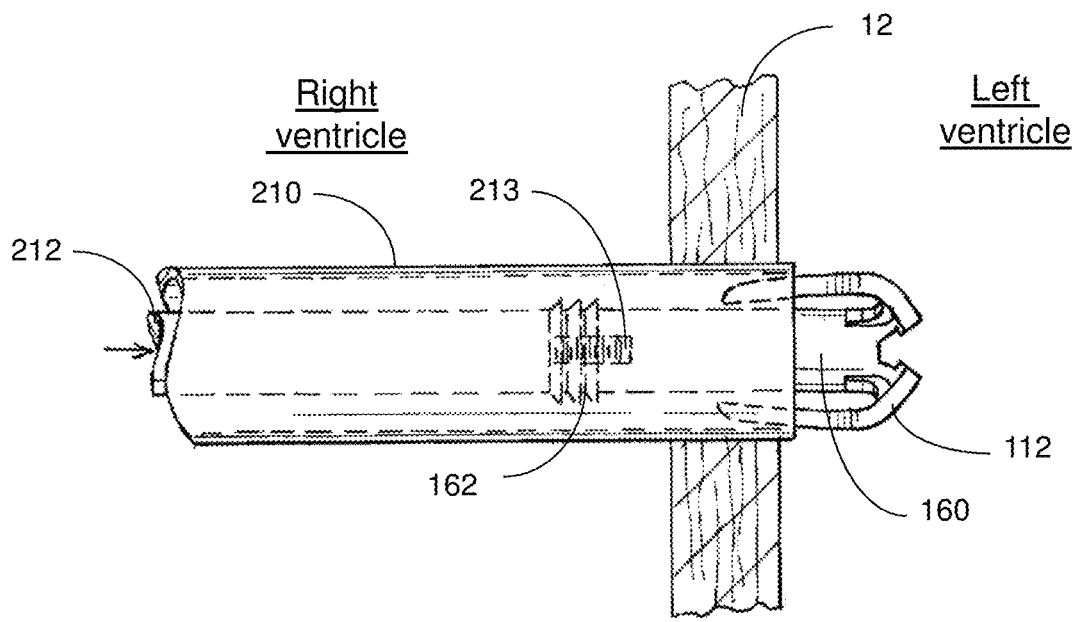
FIGS. 17A-17D depict implantation of another mechanical assist device in accordance with some embodiments.
Figure 17B:
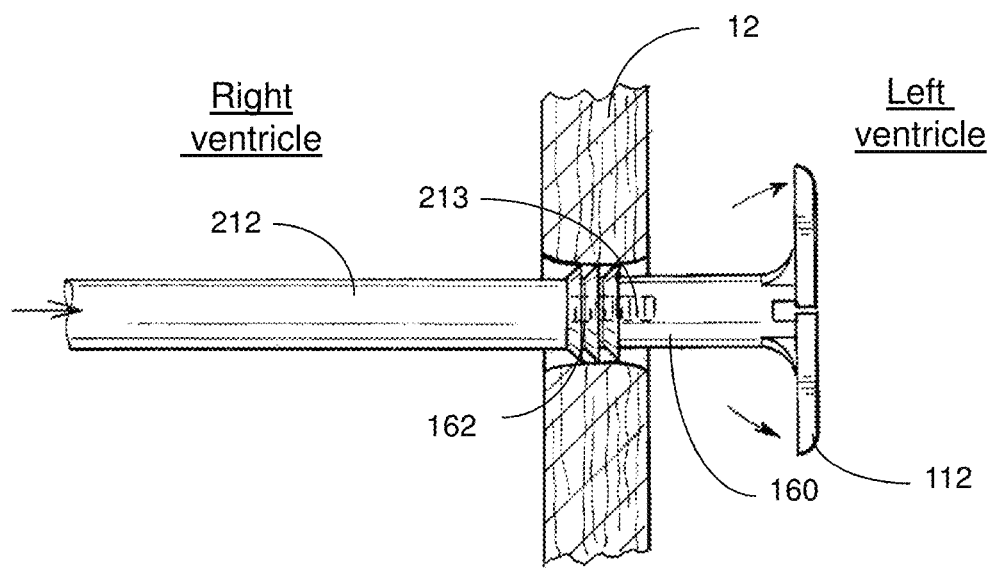

FIGS. 17A-17D illustrate an exemplary process of implanting the anchor shown in FIG. 16 across a ventricular septum 12, or another appropriate tissue wall. As shown in FIG. 17A, a positioning tool 212 is used to push the flange 112, while in its furled position, distally through the housing 210 and into the left ventricle. In this embodiment, the positioning tool 212 includes a threaded portion 213 that engages with the threaded portion of the shaft 160 so that the flange 112 may be advanced, retracted other otherwise manipulated as desired. Accordingly, when deploying the device, the flange 112 is advanced by the positioning tool 212 through the catheter housing 210. As provided in FIG. 17B, once the flange 112 is sufficiently advanced into the left ventricle, the housing 210 is withdrawn and the wings are freed to achieve an outstretched position that prevents the flange from passing back through the opening.

Figure 17C:
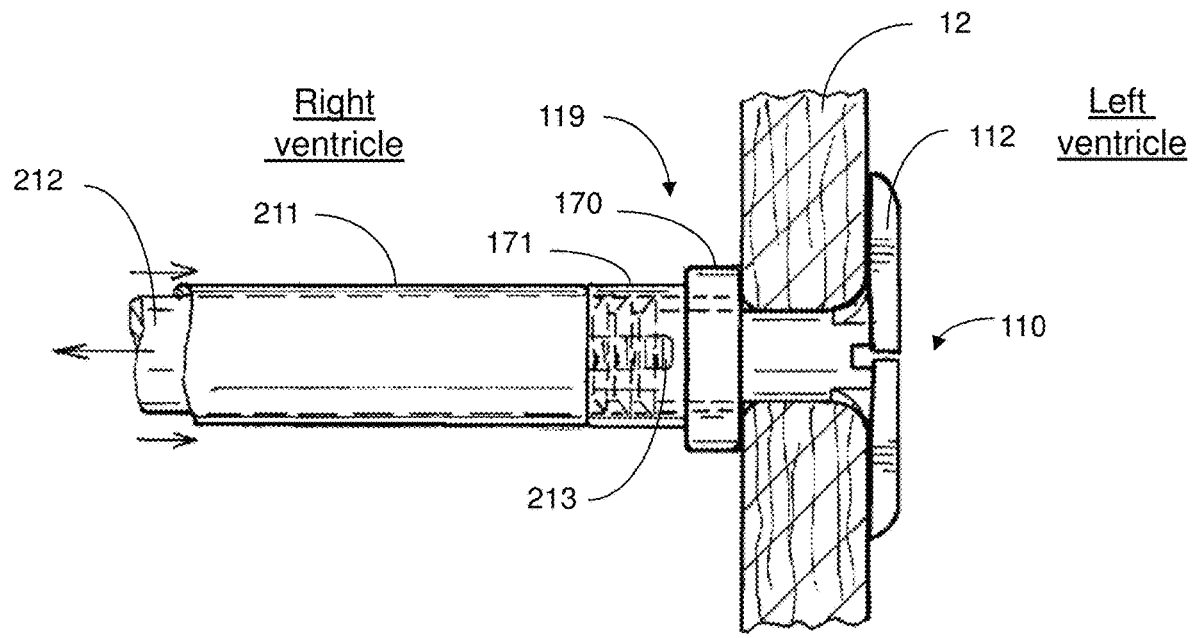

FIG. 17C illustrates installation of the anchoring member 119 with the flange 112. In this embodiment, the anchoring member 119 and the flange 112 form a seal between the left and right ventricles so as to prevent or otherwise mitigate the occurrence of a shunt through the opening formed across the ventricular septum. In this embodiment, as shown by the solid arrows in FIG. 17C, the flange 112 is pulled back by the positioning tool 212 in a proximal direction and the anchoring member 119 is pushed forward by a positioning sheath 211 in a distal direction, sandwiching the ventricular septum 12 therebetween.

Once a preferred level of compressive force is reached, for example, to maintain the anchoring member 119 and flange 112 in place while obstructing fluid flow between the ventricles, these components may be locked or otherwise firmly secured together via mutual coupling of the protruding teeth 162 and the recesses 172, securing the anchor 110 in place.

Figure 17D:
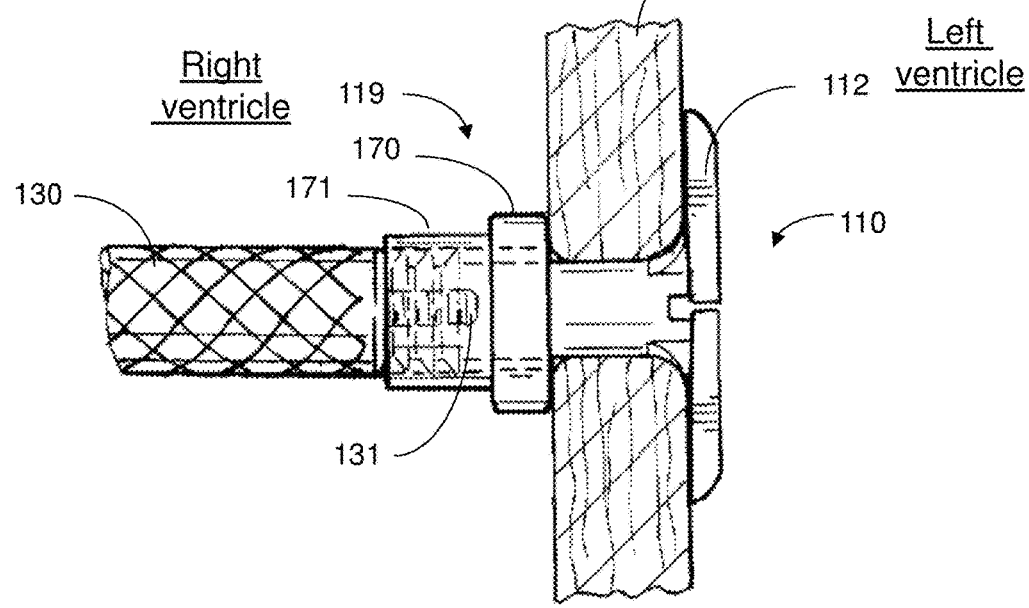

FIG. 17D illustrates the actuator 130 attached or otherwise coupled to the anchor 110, via the anchoring member 119. In this embodiment, the positioning tool 212 is withdrawn (e.g., unscrewed, decoupled) from the shaft 160, and replaced with the actuator 130. When the actuator 130 is suitably activated, the flange 112 moves a desirable amount of the septal wall so as to mimic natural pumping action of the body. Similar to embodiments described above, the actuator 130 may be easily removed from the anchoring member 119 and/or replaced. Once the actuator 130 is removed, in some cases, the anchoring member 119 and flange 112 may be left in place.

In another embodiment, the anchor(s) may include a flexible member 182 which may be altered in shape so as to be used as a flange when in a deployed state. The flexible member 182 may, in some cases, exhibit a suitable degree of elasticity, providing a spring-back force when deformed in a particular manner.

Accordingly, for some embodiments, when the flexible member 182 is altered in shape to be used as a flange for anchoring the overall device to the ventricular septum 12, the compressive force applied to the septal wall may be sufficient to form a seal between the left ventricle and the opening through the septum leading to the left ventricle.

Figure 18:
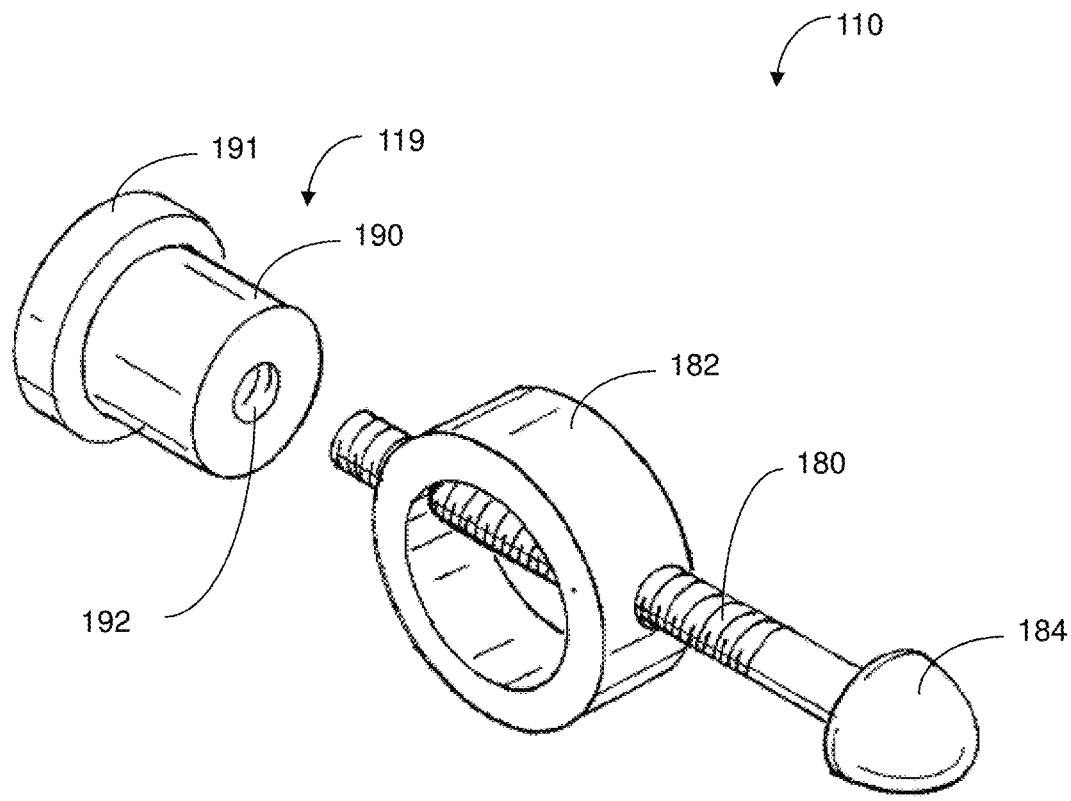
FIG. 18 illustrates a perspective view of another anchor for use in a mechanical assist device in accordance with some embodiments.

FIG. 18 illustrates a two-piece anchor 110 that includes a threaded shaft 180 having a flexible member 182 mounted thereon and extending along a substantial portion of the shaft 180, and a probe end 184 to facilitate advancement of the anchor during surgical implantation. The probe end 184 may also act as a barrier to prevent the flexible member 182 from being pushed off of the threaded shaft 180.

The flexible member 182 may include any suitable material. In some embodiments, the flexible member 182 may exhibit elastic characteristics, for example, may return to its initial shape upon release of a deforming force. For example, the flexible member 182 may include an elastomer, rubber, polyurethane, silicone, polymeric materials, spring/coiled configuration, or any other appropriate material.

In this embodiment, the anchor 110 further includes an anchoring member 119 provided as a nut having a distal portion 190 and a proximal portion 191. Here, the inner surface of the nut includes a threaded portion 192, complementary with the threaded portion of the shaft 180, for mutual engagement.

Accordingly, the anchoring member 119 may be screwed on to the shaft 180 such that the distal portion 190 pushes up against or otherwise is able to manipulate the flexible member 182, as described further below. In contrast with the embodiment depicted in FIG. 16, the proximal portion 191 of the anchoring member 119 may be slightly larger in width/diameter than the distal portion 190. Though, it can be appreciated that any suitable arrangement may be employed.

FIGS. 19A-19D depict another exemplary process of implanting the anchor of FIG. 18 across a ventricular septum 12, or another appropriate tissue wall. In this embodiment, the anchor 110 is advanced through the small passageway provided by the catheter housing 210 and the flexible member 182 is compressed between the probe end 184 and the anchoring member 119 to form a suitable flange against the septal wall.

Figure 19A:
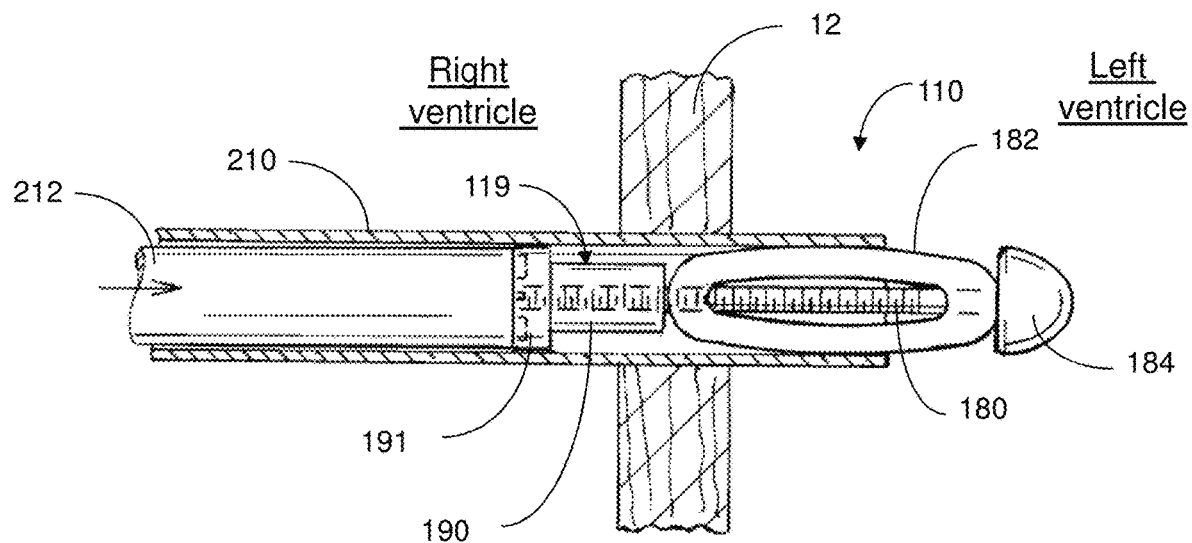
FIGS. 19A-19D show implantation of another mechanical assist device in accordance with some embodiments.

As shown in FIG. 19A, the anchoring member 119 is screwed on to the threaded shaft 180 and the positioning member 212 pushes the flexible member 182 together with the shaft 180 through the catheter housing 210. In some embodiments, a sheath or catheter housing is employed to suitably place the anchor 110, though, in other embodiments, a sheath or catheter housing is not required for placement thereof.

Figure 19B:
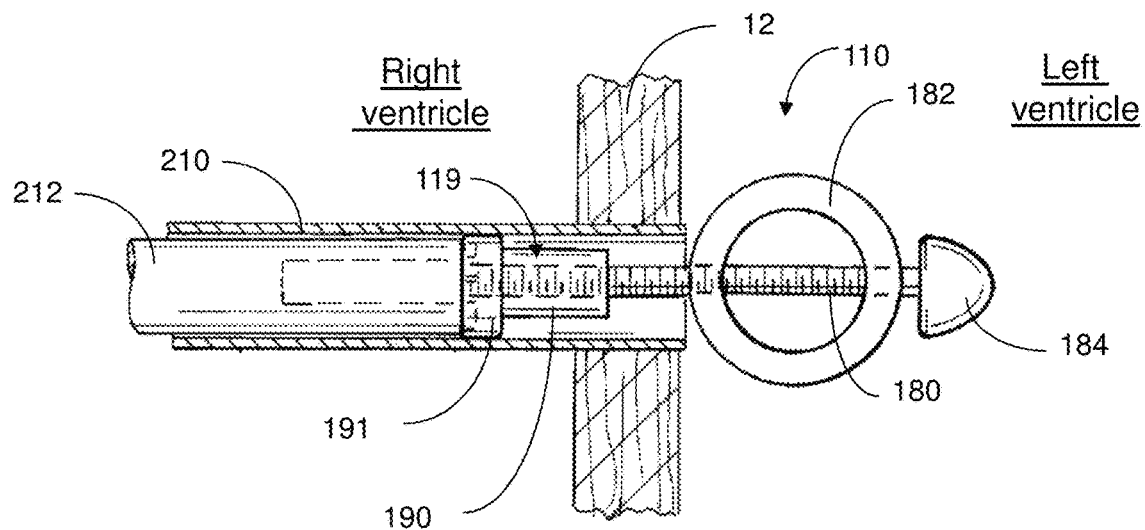
Figure 19C:
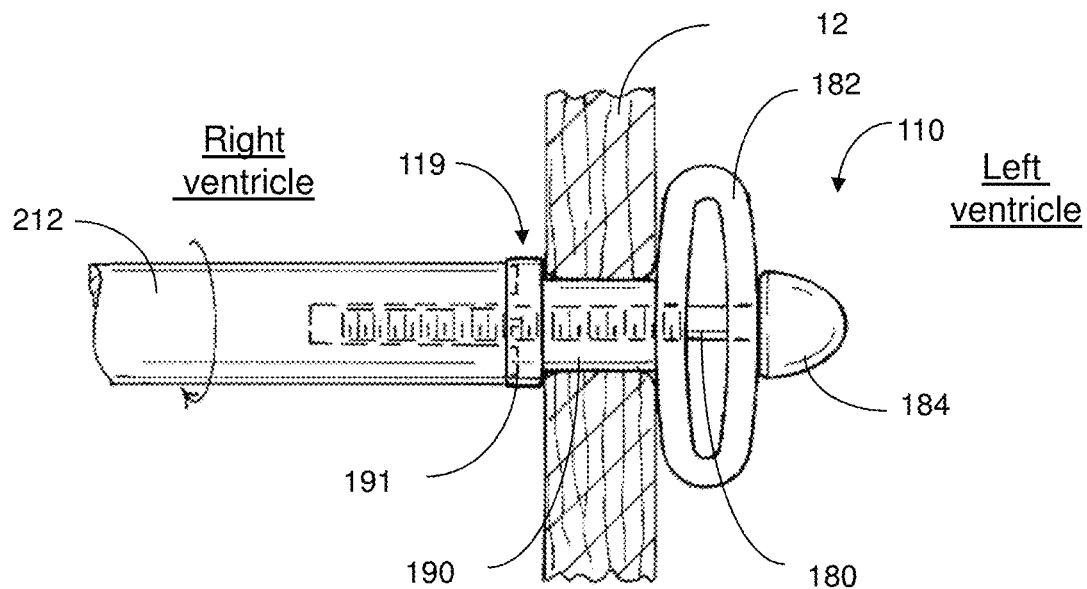

FIG. 19B shows the flexible member 182 having been sufficiently advanced into the left ventricle so as to clear the distal end of the catheter housing 210. The flexible member 182, having elastic characteristics, returns back to its original shape, shown in this embodiment to be circular. It can be appreciated that the flexible member may have any suitable natural resting shape.

In some embodiments, the positioning tool 212 is coupled to the anchoring member 119, to allow the anchoring member 119 to be moved (e.g., screwed) back and forth along the threaded shaft 180. As further shown in FIG. 19C, the catheter housing 210 is withdrawn and the anchoring member 119 is screwed further in a distal direction toward the probe end 184, compressing the flexible member 182 therebetween. This causes the flexible member 182 to deform and take on a flange-like shape that covers a substantial area of the ventricular septum 12, for actuation thereof. In accordance with aspects of the present disclosure, the biasing force from the flexible member 182 against the septal wall forms a seal preventing or otherwise obstructing fluid flow between the ventricles.

Figure 19D:
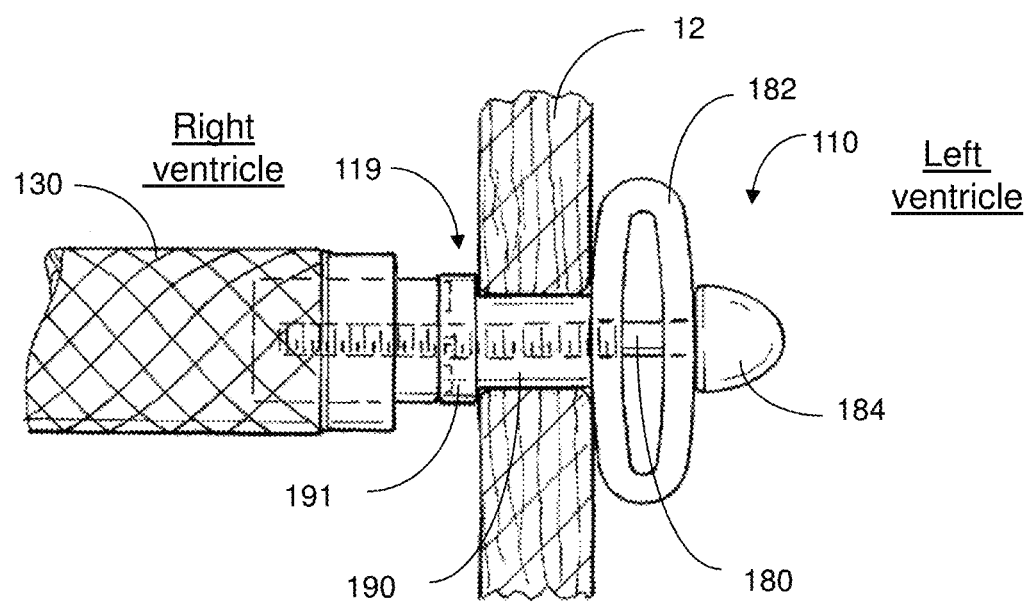

FIG. 19D shows the actuator 130 coupled to the anchor 110, via the anchoring member 119. Similar to other embodiments described herein, the positioning tool 212 may be withdrawn from the shaft 160, and replaced with the actuator 130. The actuator 130 may, in turn, also be replaced or removed from the site of implantation. Upon activation of the actuator 130, the flexible member 182, having taken on a flange-like conformation, moves the septal wall in a desirable manner.

Having thus described several aspects of at least one embodiment of this invention, it is to be appreciated various alterations, modifications, and improvements will readily occur to those skilled in the art. For example, the devices described herein may be adapted for use in medical or non-medically related applications. Such alterations, modification, and improvements are intended to be part of this disclosure, and are intended to be within the spirit and scope of the invention. Accordingly, the foregoing description and drawings are by way of example only.

What is claimed is:

1. A device for providing mechanical assistance to an organ, the device comprising:
   a first anchor adapted to engage with a first wall region of the organ;
   a second anchor adapted to engage with a second wall region of the organ; and
   an actuator coupled with the first anchor and the second anchor, the actuator adapted to move the first and second anchors relative to one another repeatedly between a contracted position where the anchors are moved toward each other to draw the first and second wall regions of the organ toward each other and an extended position where the anchors are moved away from each other relative to the contracted position to move the first and second wall regions away from each other;
   wherein the actuator is adapted to expand along a radial direction and contract along a longitudinal direction to draw the first and second wall regions towards each other and to assist ejection of fluid from a chamber defined at least in part by the first and second wall regions;
   wherein the first and second anchors are configured to withstand a force exerted by the actuator during radial expansion and longitudinal contraction;
   wherein the first and second anchors have different structures.

2. The device of claim 1, wherein the actuator is located between the first and second anchors.

3. The device of claim 1, wherein at least one of the first anchor and the second anchor is configured to be retracted from engagement with the respective wall region of the organ.

4. The device of claim 1, wherein at least one of the first anchor and the second anchor is configured to form a seal with the respective wall region of the organ.

5. The device of claim 1, wherein at least one of the first anchor and the second anchor includes a flange for securing the anchor to the respective wall region of the organ.

6. The device of claim 5, wherein at least one of the first anchor and the second anchor includes an anchoring member constructed and arranged to couple with the flange for securing the anchor to the respective wall region of the organ.

7. The device of claim 6, wherein the anchoring member and the flange are constructed and arranged to provide compressive force on opposing sides of the respective wall region of the organ.

8. The device of claim 5, wherein at least one of the first anchor and the second anchor includes at least one suture for securing the flange to the respective wall region of the organ.

9. The device of claim 5, wherein the flange is adapted to be placed in an undeployed position for installation of the anchor to the respective wall region of the organ and a deployed position for securing the anchor to the respective wall region of the organ.

10. The device of claim 1, wherein at least one of the first anchor and the second anchor includes a compartment for receiving fluid, and the compartment is adapted to expand so as to engage with the respective wall region of the organ.

11. The device of claim 1, wherein the first anchor is constructed and arranged to be secured at an inner wall surface of a left ventricle.

12. The device of claim 1, wherein the second anchor is constructed and arranged to be secured at a wall surface of a right ventricle.

13. The device of claim 1, wherein the second anchor includes a fastener having a first fastening component and a second fastening component, each of the fastening components having surfaces complementary to one another.

14. The device of claim 13, wherein the first fastening component includes threaded bolt having a lumen therethrough and the second fastening component includes a threaded nut, wherein the threads of each of the bolt and the nut are complementary to one another.

15. The device of claim 1, wherein the actuator includes a compartment for receiving an inflow of fluid, and the compartment is adapted to contract along a longitudinal direction and expand in a radial direction to the contracted position upon receiving the inflow of fluid.

16. The device of claim 15, wherein the compartment is adapted to extend along the longitudinal direction and contract in the radial direction to the extended position upon outflow of the fluid from the compartment.

17. The device of claim 15, wherein the compartment includes a bladder and a mesh surrounding the bladder.

18. The device of claim 17, wherein the mesh is constructed and arranged to guide contraction of the bladder along the longitudinal direction and expansion of the bladder along the radial direction, upon the bladder receiving the fluid.

19. The device of claim 15, further comprising a pumping apparatus for forcing the fluid into and out of the compartment.

20. The device of claim 15, further comprising a reservoir for supplying the fluid to the compartment.

21. The device of claim 20, wherein the reservoir is constructed and arranged to be located inside the body during use.

22. The device of claim 15, further comprising a valve for regulating flow of fluid into and out of the compartment.

23. The device of claim 1, further comprising a sensor for sensing information from the organ or information from the actuator during use.

24. The device of claim 23, wherein the sensor is configured to sense electrocardiogram information from the organ.

25. The device of claim 23, further comprising a controller configured to cause the actuator to move the first and second anchors according to a pattern based on the sensed information.

26. The device of claim 1, further comprising a biocompatible coating disposed over at least one of the first anchor, the second anchor and the actuator.

27. The device of claim 1, wherein the actuator is configured to form an inflation profile in the contracted position.

28. The device of claim 27, wherein, in the contracted position, a first cross-sectional diameter located at a middle of the actuator is greater than a second cross-sectional diameter located on first and second opposing ends of the actuator.

29. The device of claim 28, wherein, in the extended position, the first and second cross-sectional diameters are substantially the same.

30. A method of using a device for providing mechanical assistance to an organ, the method comprising:

engaging a first anchor with a first wall region of the organ;

engaging a second anchor with a second wall region of the organ; and operating an actuator coupled with the first anchor and the second anchor to move the first and second anchors relative to one another repeatedly between a contracted position where the anchors are moved toward each other to draw the first and second wall regions of the organ toward each other and an extended position where the anchors are moved away from each other relative to the contracted position to move the first and second wall regions away from each other, wherein the actuator is adapted to expand along a radial direction and contract along a longitudinal direction to draw the first and second wall regions towards each other and to assist ejection of fluid from a chamber defined at least in part by the first and second wall regions, wherein the first and second anchors are configured to withstand a force exerted by the actuator during radial expansion and longitudinal contraction, wherein the first and second anchors have different structures.

31. The method of claim 30, wherein engaging the first anchor with the first wall region of the organ includes inserting the first anchor through the second wall region and then into the first wall region.

* * * * *